US011878048B2

(12) United States Patent
Rauner et al.

(10) Patent No.: US 11,878,048 B2
(45) Date of Patent: Jan. 23, 2024

(54) USE OF THE EXTRACELLULAR DOMAIN OF TRANSFERRIN RECEPTOR 2 FOR THE DIAGNOSIS AND TREATMENT OF PRIMARY OR SECONDARY SCLEROSING DISEASES

(71) Applicant: Kymab Limited, Cambridge (GB)

(72) Inventors: Martina Rauner, Dresden (DE); Lorenz C. Hofbauer, Dresden (DE); Uwe Platzbecker, Dresden (DE); Ulrike Baschant, Dresden (DE)

(73) Assignee: Kymab Limited, Cambridge (GB)

( * ) Notice: Subject to any disclaimer, the term of this patent is extended or adjusted under 35 U.S.C. 154(b) by 401 days.

(21) Appl. No.: 16/622,616

(22) PCT Filed: Jun. 14, 2018

(86) PCT No.: PCT/EP2018/065846
§ 371 (c)(1),
(2) Date: Dec. 13, 2019

(87) PCT Pub. No.: WO2018/229210
PCT Pub. Date: Dec. 20, 2018

(65) Prior Publication Data
US 2020/0215154 A1 Jul. 9, 2020

(30) Foreign Application Priority Data
Jun. 14, 2017 (EP) ..................................... 17176043

(51) Int. Cl.
*A61K 38/17* (2006.01)
*C07K 14/705* (2006.01)
*G01N 33/68* (2006.01)

(52) U.S. Cl.
CPC ....... *A61K 38/177* (2013.01); *G01N 33/6893* (2013.01)

(58) Field of Classification Search
None
See application file for complete search history.

(56) References Cited

U.S. PATENT DOCUMENTS

| 8,461,155 B2 | 6/2013 | Wu |
| 2002/0039567 A1 | 4/2002 | Wallimann et al. |
| 2009/0137416 A1 | 5/2009 | Fandl |
| 2016/0176956 A1 | 6/2016 | Cong |
| 2019/0297861 A1 | 10/2019 | Williams |
| 2021/0214456 A1 | 7/2021 | Rauner et al. |

FOREIGN PATENT DOCUMENTS

| EP | 3415527 A1 | 12/2018 |
| EP | 3581196 A1 | 12/2019 |
| WO | 2008003103 A2 | 1/2008 |
| WO | 2008003103 A3 | 4/2008 |
| WO | 2010/056981 A2 | 5/2010 |
| WO | 2010/056981 A3 | 9/2010 |
| WO | 2014081955 A1 | 5/2014 |
| WO | 2015103072 A1 | 7/2015 |
| WO | 2015107075 A1 | 7/2015 |
| WO | 201639796 A2 | 3/2016 |
| WO | 201639796 A3 | 3/2016 |
| WO | 2016098079 A2 | 6/2016 |
| WO | 2016098079 A3 | 8/2016 |
| WO | 2017191437 A1 | 11/2017 |
| WO | 2018011573 A1 | 1/2018 |
| WO | 201822910 A1 | 12/2018 |
| WO | 2018229210 A1 | 12/2018 |
| WO | 2019238713 A2 | 12/2019 |
| WO | 2019238713 A3 | 2/2020 |

OTHER PUBLICATIONS

Adamis, A.P. et al. (Jan. 2006, e-pub. Dec. 15, 2005). "Changes in Retinal Neovascularization After Pegaptanib (Macugen) Therapy in Diabetic Individuals," Ophthalmology 113(1):23-28.
Agarwal, S. et al. (Dec. 8, 2016). "mTOR Inhibition and BMP Signaling Act Synergistically to Reduce Muscle Fibrosis and Improve Myofiber Regeneration," JCI insight 1(20):e89805, 12 pages.
Altamura, S. et al. (Aug. 5, 2014). "Resistance of Ferroportin to Hepcidin Binding Causes Exocrine Pancreatic Failure and Fatal Iron Overioad," Cell Metabolism 20(2):359-367.
Andriopoulos, B. Jr. et al. (Apr. 2009, e-pub. Mar. 1, 2009). "BMP-6 Is a Key Endogenous Regulator of Hepcidin Expression and Iron Metabolism," Nature Genetics 41(4):482-487, 16 pages.
Anonymous (Jan. 18, 2012). "Trabecular Thickness (Tb.Th), Trabecular Spacing (Tb.Sp), Trabecular No. (Tb.N)," retrieved from http://microctworld.net/trabecular-thickness-tb-th-trabecular-spacing-tb-sD-trabecularnumber-tb-n/, last visited Aug. 12, 2020, 6 pages.
Anonymous: (Dec. 23, 2016). "TFRC/TFR2 Monoclonal Antibody, Clone CY-TFR," retrieved from the internet http://www.abnova.com/rotocol_pdf/DS_MAB6780.pdf, last visited Sep. 18, 2018, 1 page.
Babitt, J.I. et al. (May 2006, e-pub. Apr. 9, 2006). "Bone Morphogenetic Protein Signaling by Hemojuvelin Regulates Hepcidin Expression," Nature Genetics 38(5):531-539.
Babraham Bioinformatics "Welcome to Babraham Bioinformatics," retrieved from http://www.bioinformatics.babraham.ac.uld, last visited Aug. 12, 2020, 1 page.
Bao, Q. et al. (Nov. 2018, e-pub. Jul. 9, 2018). "Disruption of Bone Morphogenetic Protein Type IA Receptor in Osteoblasts Impairs Bone Quality and Bone Strength in Mice," Cell and Tissue Research 374(2):263-273.

(Continued)

*Primary Examiner* — Christine J Saoud
*Assistant Examiner* — Jon M Lockard
(74) *Attorney, Agent, or Firm* — MORRISON & FOERSTER LLP

(57) ABSTRACT

The invention relates to a protein for use in diagnosing and treating primary or secondary sclerosing diseases, a fusion protein, and nucleotide sequence and a vector, and to a pharmaceutical composition for use in diagnosing and treating primary or secondary sclerosing diseases.

Figure 1:
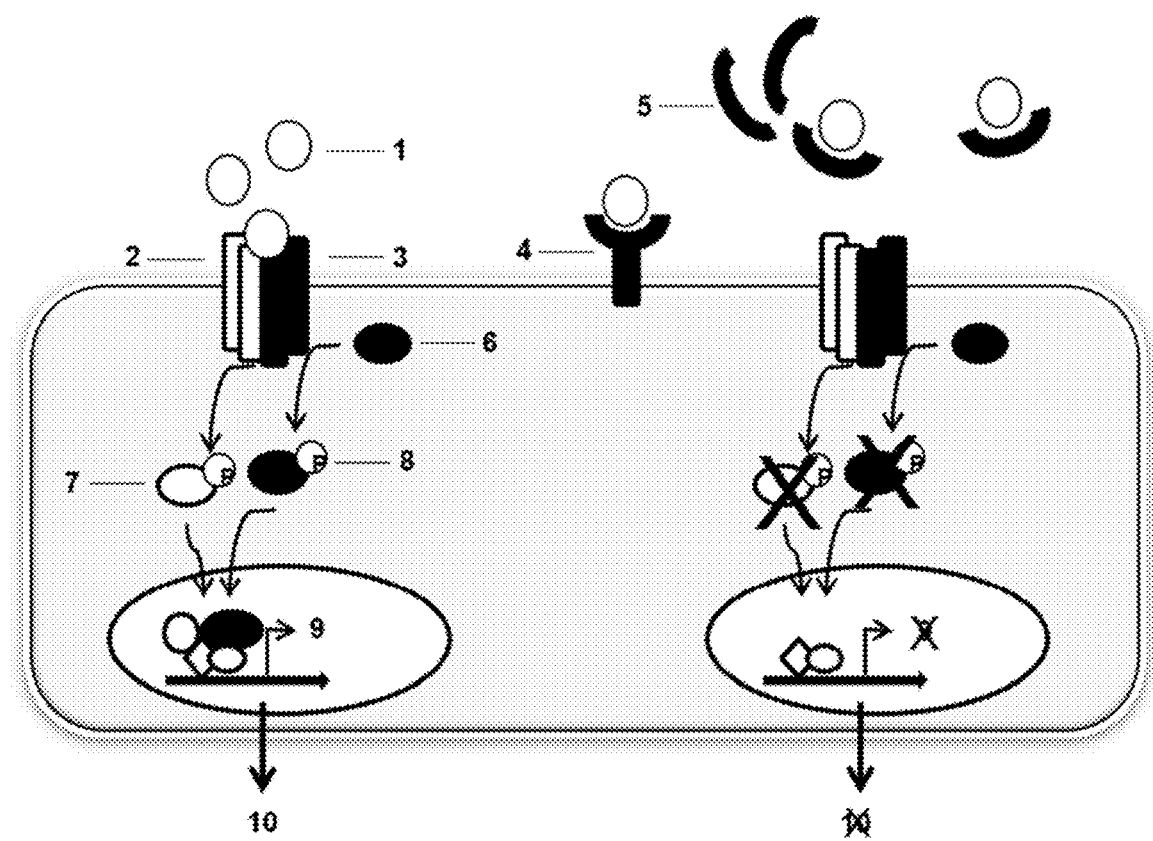

5 Claims, 4 Drawing Sheets
Specification includes a Sequence Listing.

(56) References Cited

OTHER PUBLICATIONS

Baschant, U. et al. (May 13-16, 2017, e-pub. May 11, 2017). "The Iron-Sensing Receptor TFR2 Regulates Osteoclastogenesis," Abstracts of the ECTS Congress 2017 Edition, Abstract No. P-OCBER-7, p. S43, 44th Europear Calcified Tissue Societyy Congress, 100:S1-S174.

Basse J.H.D. et al. (Apr. 20, 2010, e-pub. Apr. 5, 2010). "Optimal Bone Strength and Mineralization Requires the Type 2 Iodothyronine Deiodinase in Osteoblasts," Pro. Nat. Acad. Sci. USA 107(16):7604-7609.

Berger, S.L. (1987). "Isolation of Cytoplamic RNA: Ribonucleoside-Vanadyl Complexes," Methods in Enzymology 152:227-234.

Biswas, S. et al. (May 31, 2018, e-pub. May 31, 2018). "BMPRIA Is Required for Osteogenic Differentiation and RANKL Expression in Adult Bone Marrow Mesenchymal Stromal Cells," Scientific Reports 8(1):8475, 14 pages.

Calzolari, A. et al. (Apr. 1, 2010). "Transferrin Receptor2 is Frequently and Highly Expressed in Glioblastomas," Translational Oncology 3(2):123-134.

Dalzolari, A. et al. (Nov. 1, 2006, e-pub. Oct. 17, 2006). "TfR2 Localizes in Lipid Raft Domains and is Released in Exosomes to Activate Signal Transduction Along the MAPK Pathway," Journal of Cell Science 119 (pt21):4486-4498.

Camaschella, C. et al. (May 2000). "The Gene IFR2 Is Mutated in a New Type of Haemochromatosis Mapping to 7q22," Nature Genetics 25(1):14-15.

Canali, S. et al. (2017). "Bone Morphogenetic Protein 2 Controls Iron Homeostasis in Mice Independent of Bmp6," American Journal of Hematology Am J. Hematol. 92:1204-1213.

Cartellieri, M. et al. (Aug. 12, 2016). "Switching Car T Cells On and Off: A Novel Modular Platform for Retargeting of T Cells to AML Blasts," Blood Cancer J. 6(8):e458, 8 pages.

Chakkalakal, S.A. et al. (Sep. 2016, e-pub, Mar. 12, 2016). "Palovarotene Inhibits Heterotopic Ossification and Maintains Limb Mobility and Growth in Mice With the Human ACVR1(R206H) Fibrodysplasia Ossificans Progressiva (FOP) Mutation," Journal of Bone and Mineral Research 31(9):1666-1675, 21 pages.

Chothia, C. et al. (Aug. 20, 1987). "Canonical Structures for the Hypervariable Regions of Immunoglobulins," J. Mol. Biol. 196(4):901-917.

Colditz, J. et al. (Feb. 1, 2018). "Dickkopf-1 (DKK-1) Plays Distinct Pathogenic Roles in Estrogen-Deficiency vs. Glucocorticoid-Induced Bone Loss," Osteologie 27(1):A5.

Croons, V. et al. (Jun. 2009, e-pub, Mar. 23, 2009). "The Protein Synthesis Inhibitor Anisomycin Induces Macrophage Apoptosis in Rabbit Atherosclerotic Plaques Through P38 Mitogen-Activated Protein Kinase," The Journal of Pharmacology and Experimental Therapeutics 329(3):856-864.

D'Alessio, F. et al. (Nov. 2012, e-pub. Jun. 21, 2012). "The Hemochromatosis Proteins HFE, TfR2, and HJV Form a Membrane-Associated Protein Complex for Hepcidin Regulation," Journal of Hepatology 57(5):1052-1060.

DiGiammarino, E. et al. (2012). "Design and Generation of DVD-IgTM Molecules for Dual-Specific Targeting," Meth. Mo. Biol. 889:145-156.

Doyard, M. et al. (Feb. 1, 2016). "Decreased Bone Formation Explains Osteoporosis in a Genetic Mouse Model of Hemochromatosiss," PLoS One 11(2):e0148292, 10 pages.

Fielding, R.A. et al. (May 11, 2017). "Abstracts of the ECTS Congress 2017 Edition," Calcified Tissue International 100(1):1-174.

Fleming, R.E. et al. (Aug. 6, 2002, e-pub. Jul. 19, 2002). "Targeted Mutagenesis of the Murine Transferrin Receptor-2 Gene Produces Hemochromatosis," Proc. Natl. Acad. Sci. USA 99(16):10653-10658.

Forejtnikova, H. et al. (Dec. 9, 2010, e-pub. Sep. 8, 2010). "Transferrin Receptor 2 Is a Component of the Erythropoietin Receptor Complex and Is Required for Efficient Erythropoiesis," Blood 116(24):5357-5367.

Forsberg, J.A. et al. (May 2009). "Heterotopic Ossification in High-Energy Wartime Extremity Injuries: Prevalence and Risk Factors," The Journal of Bone and Joint Surgery 91(5):1084-1091.

Fransen, M. et al. (Sep. 9, 2006, e-pub. Aug. 2, 2006). "Safety and Efficacy of Routine Postoperative Ibuprofen for Pain and Disability Related to Ectopic Bone Formation After Hip Replacement Surgery (HIPAID): Randomised Controlled Trial," BMJ 333(7567):519, 5 pages.

Freshney, R.I. (2005). Culture of Animal Cells: A Manual of Basic Technique, 65th Edition, John Wiley & Sons, Inc. pp. 115-128. TOC, 12 pages.

Fujiwara, T. et al. (Feb. 1, 2014). "SU0262—Iron Homeostasis Is Critical for Osteoclast Differentiation," American Society for Bone and Mineral Research 29(sup. 1):S285, 498 pages.

Guggenbuhl, P. et al. (Aug. 2011, e-pub. Oct. 26, 2010). "Bone Status in a Mouse Model of Genetic Hemochromatosis," Osteoporosis International 22(8):2313-2319.

Guggenbuhl, P. et al. (Dec. 2005, e-pub. Jun. 1, 2005). "Bone Mineral Density in Men With Genetic Hemochromatosis and HFE Gene Mutation," Osteoporosis International 16(12):1809-1814.

Herrmann, T. et al. (Jan. 2004, e-pub. Nov. 15, 2003). "Iron Overload in Adult Hfe-Deficient Mice Independent of Changes in the Steady-State Expression of the Duodenal Iron Transporters DMT 1 and Ireg1/ferroportin," Journal of Molecular Medicine 82(1):39-48.

Hino, K. et al. (Sep. 1, 2017, e-pub. Jul. 31, 2017). "Activin-A Enhances mTOR signaling to Promote Aberrant Chondrogenesis in Fibrodysplasia Ossificans Progressiva," The Journal of Clinical Investigation 127(9):3339-3352.

Hogan, B.L.M. (Jul. 1, 1996). "Bone Morphogenetic Proteins: Multifunctional Regulators of Vertebrate Development," Genes & Development 10(13):1580-1594.

Imel, E.A. et al. (May 2016, e-pub. Mar. 8, 2016). "Serum Fibroblast Growth Factor 23, Serum Iron and Bone Mineral Density in Premenopausal Women," Bone 86:98-105, 22 pages.

International Preliminary Report and Patentability, dated Dec. 17, 2019, for PCT Application No. PCT/EP2018/065846, filed Jun. 14, 2018, 5 pages.

International Search Report and Written Opinion, dated Jan. 8, 2020, for PCT Application No. PCT/EP2019/065257, 31 pages.

International Search Report and Written Opinion, dated Sep. 26, 2018, for PCT Application No. PCT/EP2018/065846, filed Jun. 14, 2018, 6 pages.

Johnson, M.B. et al. (Dec. 15, 2004, e-pub. Aug. 19, 2004). "Diferric Transferrin Regulates Transferrin Receptor 2 Protein Stability," Blood 104(13):4287-4293.

Kabat, E. A. et al., "Sequences of Proteins of Immunological Interest," Fifth Edition, U.S. Department of Health and Human Services, NIH Publication No. 91-3242 (1991), 83 pages.

Kabat, E.A. et al. (1971). "Attempts to Locate Complementarity-Determining Residues in the Variable Positions of Light and Heavy Chains," Ann NY Acad Sci 190:382-391.

Kamiya, N. et al. (Feb. 2010). "Wnt Inhibitors Dkk1 and Sost Are Downstream Targets of BMP Signaling Through The Type IA Receptor (BMPRIA) in osteoblasts," Journal of Bone and Mineral Research 25(2):200-210.

Kamiya, N. et al. (Nov. 2008, e-pub. Oct. 16, 2008). "BMP Signaling Negatively Regulates Bone Mass Through Sclerostin by Inhibiting the Canonical Wnt Pathway," Development 135(22):3801-3811, 23 pages.

Kamiya, N. et al. (Oct. 22, 2011, e-pub. Sep. 17, 2011). "Loss-of-Function of ACVR1 in Osteoblasts Increases Bone Mass and Activates Canonical Wnt Signaling Through Suppression of Wnt Inhibitors SOST and DKK1," Biochemical and Biophysical Research Communications 414(2):326-330, 12 pages.

Karpinski, J. et al. (Apr. 2016, e-pub. Feb. 22, 2016). "Directed Evolution of a Recombinase That Excises the Provirus of Most HIV-1 Primary Isolates With High Specificity," Nat Biotechnol. 34(4):401-409.

Keller, S. et al. (May 2004, e-pub. Apr. 4, 2004). "Molecular Recognition of BMP-2 and BMP Receptor IA," Nature Structural & Molecular Biology 11(5):481-488.

(56) References Cited

OTHER PUBLICATIONS

Kiper, P.O.S. et al. (Jun. 30, 2016). "Cortical-Bone Fragility—Insights from sFRP4 Deficiency in Pyle's Disease," The New England Journal of Medicine 374(26):2553-2562, 14 pages.

Koch, P.-S. et al. (Jan. 26, 2017, e-pub. Nov. 30, 2016). "Angiocrine Bmp2 Signaling in Murine Liver Controls Normal Iron Homeostasis," Blood 129(4):415-419, 8 pages.

Kölbl, O. et al. (Nov. 7, 2003) Prevention von heterotopen Ossifikationen nach Totalendoprothese des Huftgelenks [Prevention of Heterotopic Ossification Following Total Replacement of the Hip Joint]. Deutsches Arzteblatt [German Medical Journal] 45:2944-2954. English Abstract.

Lee, S.J. et al. (Feb. 2010, e-pub. Dec. 29, 2009). "Immunomodulator Therapy: Monoclonal Antibodies, Fusion Proteins, Cytokines, and Immunoglobulins," J Allergy Clin Immunol. 125(2Suppl. 2):S314-S323.

Lefranc, M.P. (Nov. 1, 1997). "Unique Database Numbering System for Immunogenetic Analysis," Immunol. Today 18(11):P509.

Li, X. et al. (Jun. 2008, e-pub. Feb. 11, 2008). "Targeted Deletion of the Sclerostin Gene in Mice Results in Increased Bone Formation and Bone Strength," Journal of Bone and Mineral Research 23(6):860-869.

Liu, C. et al. (Feb. 4, 2014). "Arginine-Terminated Generation 4 PAMAM Dendrimer as an Effective Nanovector for Functional siRNA Delivery In Vitro and In Vivo," Bioconjug Chem 25(3):521-532.

Liu, X. et al. (Feb. 2014). "A Novel Mouse Model of Trauma Induced Heterotopic Ossification," Journal of Orthopaedic Research 32:183-188.

Lively, T.N. et al. (Jan. 2008, e-pub. Oct. 22, 2007). "Effect of Chemically Modified IL-13 Short Interfering RNA on Development of Airway Hyperresponsiveness in Mice," J Allergy Clin Immunol 121(1):88-94.

Lowery, J.W. et al. (Apr. 1, 2015, e-pub. Feb. 6, 2015). "Loss of BMPR2 Leads to High Bone Mass Due to Increased Osteoblast Activity,". Journal of Cell Science 128(7):1308-1315.

MacDonald, B.T. et al. (Sep. 2007, e-pub. Jun. 5, 2007). "Bone Mass Is Inversely Proportional to Dkk1 Levels in Mice," Bone 41(3):331-339, 18 pages.

Mayeur, C. et al. (Sep. 25, 2014, e-pub. Jul. 29, 2014). "BMP Type II Receptors Have Redundant Roles in the Regulation of Hepatic Hepcidin Gene Expression and Iron Metabolism," Blood 124(13):2116-2123.

Modzelewski, A.J. et al. (Jun. 2018, e-pub. May 10, 2018). "Efficient Mouse Genome Engineering by CRISPR-EZ Technology," Nat Protoc. 13(6):1253-1274, 58 pages.

Mootha, V.K. et al. (Jul. 2003). "PGC-1α-Responsive Genes Involved in Oxidative Phosphorylation Are Coordinately Downregulated In Human Diabetes," Nature Genetics 34(3):267-273, 10 pages.

Muckenthaler, M.U. et al. (Jan. 26, 2017). "Red Carpet for Iron Metabolism," Cell 168(3):344-361, 37 pages.

Nai, A. et al. (Jun. 2014, e-pub. Mar. 21, 2014). "The Erythroid Function of Transferrin Receptor 2 Revealed by Tmprss6 Inactivation in Different Models of Transferrin Receptor 2 Knockout Mice," Haematologica 99(6):1016-1021.

Nakamura, T. et al. (Sep. 7, 2007). "Estrogen Prevents Bone Loss Via Estrogen Receptor α and Induction of Fas Ligand in Osteoclasts," Cell 130(5):811-823.

Nemeih, E. et al. (Dec. 17, 2004, e-pub. Oct. 28, 2004). "Hepcidin Regulates Cellular Iron Efflux by Binding to Ferroportin and Inducing Its Internalization," Science 306(5704):2090-2093.

Norden, D.M. et al. (Dec. 15, 2015, e-pub. Oct. 20, 2015). "Ibuprofen Ameliorates Fatigue- and Depressive-Like Behavior in Tumor-Bearing Mice," Life Sciences 143:65-70, 15 pages.

Park, J.-W. et al. (2013, e-pub. Oct. 15, 2012). "Positive Modulation of Osteogenesis- and Osteoclastogenesis-Related Gene Expression With Strontium-Containing Microstructured Ti Implants in Rabbit Cancellous Bone," J. Biomed. Mater. Res. Part A 2013(101A):298-306.

Paul, W.E. ed. (1989). Fundamental Immunology: Second Edition, Raven Press, New York, pp. 332-337.

Picke, A.-K. et al. (Feb. 1, 2018). "Sulfated Hyaluronan Enhances Bone Defect Regeneration of Diabetic Rats in Type 2 Diabetic Rats by Improving Osteoblast Function and Sclerostin Binding," Osteologie 27(1):A15-A16.

Pietras, K. et al. (Oct. 1, 2002). "Inhibition of PDGF Receptor Signaling in Tumor Stroma Enhances Antitumor Effect of Chemotherapy," Cancer Res 62(19):5476-5484.

Platzbecker, U. et al. (Oct. 2017, e-pub. Sep. 1, 2017). "Luspatercept for the Treatment of Anaemia in Patients With Lower-Risk Myelodysplastic Syndromes (PACE_MDS): A Multicentere, Open-Label Phase 2 Dose-Finding Study With Long-Term Extension Study," Lancet Oncol. 18(10):1338-1347.

Poli, M. et al. (Nov. 2010, e-pub. Jul. 15, 2010). "Transferrin Receptor 2 and HFE Regulate Furin Expression Via Mitogenactivated Protein Kinase/Extracellular Signal-Regulated Kinase (MAPK/Erk) signaling. Implications for Transferrin-Dependent Hepcidin Regulation," Haematologica 95(11):1832-1840.

Powell, L.W. et al. (Aug. 13, 2016, e-pub. Mar. 12, 2016). "Haemochromatosis," Lancet 388(10045):706-716.

Ramos, E. et al. (Apr. 2011). "Evidence for Distinct Pathways of Hepcidin Regulation by Acute and Chronic Iron Loading in Mice," Hepatology 53(4):1333-1341, 17 pages.

Rauner, M. et al. (Jan. 2019). "Transferrin Receptor 2 Controls Bone Mass and Pathological Bone Formation Via BMP and Wnt Signaling," Nature Metabolism 1(1):111-124, 35 pages.

Rauner, M. et al. (Oct. 2016, e-pub. May 13, 2016). "Increased EPO Levels Are Associated With Bone Loss in Mice Lacking PHD2 in EPO-Producing Cells," Journal of Bone and Mineral Research 31(10):1877-1887.

Regis, D. et al. (2013, e-pub. Jun. 24, 2013). "Incidence of Heterotopic Ossification After Surface and Conventional Total Hip Arthroplasty: A Comparative Study Using Anterolateral Approach and Indomethacin Prophylaxis," BioMed Research International 2013:293528, 4 pages.

Rhee, Y. et al. (May 2011). "PTH Receptor Signaling in Osteocytes Governs Periosteal Bone Formation and Intracortical Remodeling," Journal of Bone and Mineral Research 26(5):1035-1046.

Riley, J.L. (Jul. 11, 2013, e-pub. Jun. 2, 2013). "Combination Checkpoint Blockade—Taking Melanoma Immunotherapy to the Next Level," N Engl J Med. 369(2):187-189.

Rishi, G. et al. (Feb. 1, 2013, e-pub. Nov. 25, 2015). "Normal Systemic Iron Homeostasis in Mice With Macrophage-Specific Deletion of Transferrin Receptor 2," American Journal of Physiology. Gastrointestinal and Liver Physiology 310(3): G171-G180.

Rodda, S.J. et al. (Aug. 2006, e-pub. Jul. 19, 2006). "Distinct Roles for Hedgehog and Canonical Wnt Signaling in Specification, Differentiation and Maintenance of Osteoblast Progenitors," Development 133(16):3231 3244.

Roetto, A. et al. (Apr. 22, 2010, e-pub. Feb. 23, 2010.). "Comparison of 3 Tfr2-Deficient Murine Models Suggests Distinct Functions for Tfr2-α and Tfr2-β Isoforms in Different Tissues," Blood 115(16):3382-3389.

Roskoski, R. Jr. (Oct. 3, 2003). "STI-571: An Anticancer Protein-Tyrosine Kinase Inhibitor," Biochem Biophys Res Commun. 309(4):709-717.

Salbach-Hirsch, J. et al. (Feb. 1, 2018). "Glukosaminoglykan-Sulfat-Modification Stimuliert Wnt Signaling Durch Inaktivierung Dr Wnt-Inhibtoren Sklerostin und Dickkopf-1," Osteologie A39:P37. English Translation.

Sambrook, J. et al. (2012). Molecular Cloning: A Laboratory Manual (4 ed.), Cold Spring Harbor Laboratory Press, Cold Spring Harbor, N.Y., USA. TOC, 34 pages.

Sanjuan-Pla, A. et al. (Oct. 10, 2010, e-pub. Aug. 11, 2013). "Platelet-Biased Stem Cells Reside at the Apex of the Haematopoietic Stem-Cell Hierarchy," Nature 502(7470):232-236.

Shen, G.S. et al. (Jun. 2014, e-pub. Mar. 21, 2014). "Hepcidin1 Knockout Mice Display Defects in Bone Microarchitecture and Changes of Bone Formation Markers," Calcified Tissue International 94(6):632-639, 9 pages.

Shimono, K. et al. (Apr. 2011, e-pub. Apr. 3, 2011). "Potent Inhibition of Heterotopic Ossification by Nuclear Retinoic Acid Receptor γ Agonists," Nature Medicine 17(4):454-460, 18 pages.

(56) References Cited

OTHER PUBLICATIONS

Shore, E.M. et al. (May 2006, e-pub. Apr. 23, 2006). "A Recurrent Mutation in the BMP Type 1 Receptor ACVR1 Causes Inherited and Sporadic Fibrodysplasia Ossificans Progressiva," Nature Genetics 38(5):525-527.

Shore, E.M. et al. (Sep. 2008, e-pub. May 28, 2008). "Insights From a Rare Genetic Disorder of Extra-Skeletal Bone Formation, Fibrodysplasia Ossificans Progressiva (FOP)," Bone 43:427-433, 16 pages.

Spiess, C. et al. (2015, e-pub. Jan. 27, 2015). "Alternative Molecular Formats and Therapeutic Applications for Bispecific Antibodies," Mol. Immunol. 67:95-106.

Steinbicker, A.U. et al. (Oct. 13, 2011, e-pub. Aug. 12, 2011). "Perturbation of Hepcidin Expression by BMP Type 1 Receptor Deletion Induces Iron Overload in Mice," Blood 118(15):4224-4230.

Subramanian, A. et al. (Oct. 25, 2005). "Gene Set Enrichment Analysis: A Knowledge-Based Approach for Interpreting Genome-Wide Expression Profiles," Proc. Natl. Acad. Sci. USA 102(43):15545-15550.

Theurl, I. et al. (Aug. 2016, e-pub. Jul. 18, 2016). "On-Demand Erythrocyte Disposal and Iron Recycling Requires Transient Macrophages in the Liver," Nature Medicine 22(8):945-951, 27 pages.

Tsay, J. et al. (Oct. 7, 2010, e-pub. Jun. 16, 2010). "Bone Loss Caused by Iron Overload in a Murine Model: Importance of Oxidative Stress," Blood 116(14):2582-2589.

Urist, M.R. (Nov. 12, 1965). "Bone: Formation by Autoinduction," Science 150(3698):893-899.

Van Bezooijen, R.L. et al. (Mar. 15, 2004). "Sclerostin Is an Osteocyte-Expressed Negative Regulator of Bone Formation, But Not a Classical BMP Antagonist," The Journal of Experimental Medicine 199(6):805-814.

Wallace, D.F. et al. (Dec. 2009). "Combined Deletion of Hfe and Transferrin Receptor 2 in Mice Leads to Marked Dysregulation of Hepcidin and Iron Overload," Hepatology 50(6):1992-2000.

Wallace, D.F. et al. (Jul. 2005). "First Phenotypicdescription of Transferrin Receptor 2 Knockout Mouse, and the Role of Hepcidin," Gut 54(7):980-986.

Wallace, D.F. et al. (Mar. 2015, e-pub. Nov. 17, 2014). "A Critical Role for Murine Transferrin Receptor 2 in Erythropoiesisduring Iron Restriction," British Journal of Haematology 168(6):891-901.

Wang, R.-H. et al. (Dec. 2005). "A Role of SMAD4 in Iron Metabolism Through the Positive Regulation of Hepcidin Expression," Cell Metabolism 2(6):399-409.

Witcher, P.C. et al. (Jun. 7, 2018). "Sclerostin Neutralization Unleashes the Osteoanabolic Effects of Dkk1 Inhibition," JCI Insight, 14 pages.

Wolken, D.M.A. et al. (Apr. 2018). "The Obligatory Role of Activin-A in the Formation of Heterotopic Bone in Fibrodysplasia Ossificans Progressiva," Bone 109:210-217, 18 pages.

Wosczyna, M.W. et al. (May 2012). "Multipotent Progenitors Resident in the Skeletal Muscle Interstitium Exhibit Robust BMP-Dependent Osteogenic Activity and Mediate Heterotopic Ossification," J Bone Miner Res. 27:1004-1017, 23 pages.

Yin, H. et al. (Apr. 18, 2008, e-pub. Mar. 4, 2008). "Characterization of Ligand-Binding Properties of the Human BMP Type II Receptor Extracellular Domain," Journal of Molecular Biology 378(1):191-203.

Yu, C. et al. (Feb. 2017, e-pub. Dec. 14, 2016). "Advanced Oxidation Protein Products Induce Apoptosis, and Upregulate Sclerostin and RANKL Expression, in Osteocytic MLO-Y4 Cells Via JNK/p38 MAPK Activation," Molecular Medicine Reports 15(2):543-550.

Yu, P.B. et al. (Jan. 2008, e-pub. Nov. 18, 2007). "Dorsomorphin Inhibits BMP Signals Required for Embryogenesis and Iron Metabolism," Nature Chemical Biology 4(1):33-41, 21 pages.

Zaidi, S.K. et al. (2001). "A Specific Targeting Signal Directs Runx2/Cbfa1 to Subnuclear Domains and Contributes to Transactivation of the Osteocalcin Gene," Journal of Cell Science 114:3093-3102.

Zhang, Y. et al. (Jul. 2016, e-pub. Apr. 23, 2016). "Loss of BMP Signaling Through BMPR1A in Osteoblasts Leads to Greater Collagen Cross-Link Maturation and Material-Level Mechanical Properties in Mouse Femoral Trabecular Compartments," Bone 88:74-84, 25 pages.

Rauner, M. et al. (2019, e-pub. Jan. 16, 2020). "Genetics and Future Therapy Prospects of Fibrodysplasia Ossificans Progressiva," Medizinische Genetik 31:391-396.

Testi, C. et al. (2019). "Structural Analysis of the Transferrin Receptor Multifaceted Ligand(s) Interface," Biophysical Chemistry 254:106242, 10 pages.

Vogt, T.M. et al. (Mar. 1, 2003). "Heterotypic Interactions Between Transferring Receptor and Transferrin Receptor 2," Blood 101:2008-2014.

Worthen, C. A. et al. (Mar. 6, 2014). "The Role of Hepatic Transferrin Receptor 2 in the Regulation of Iron Homeostasis in the Body," Frontiers in Pharmacology 5(34):1-8.

Deaglio, S. et al. (2002). "Structural, Functional, and Tissue Distribution Analysis of Human Transferrin Receptor-2 by Murine Monoclonal Antibodies and a Polyclonal Antiserum," Blood 100:3782-3789.

Wang, X. et al. (Mar. 22, 2018). "The Development of New Drug Targeting Hepcidin," Chinese Journal of Pharmaceutical Sciences 53(6):405-410. English Abstract, 6 pages.

SEQUENCE LISTING

```
<160> NUMBER OF SEQ ID NOS: 9

<210> SEQ ID NO 1
<211> LENGTH: 697
<212> TYPE: PRT
<213> ORGANISM: Homo sapiens

<400> SEQUENCE: 1

Arg Gly Ser Cys Gln Ala Cys Gly Asp Ser Val Leu Val Val Ser Glu
1               5                   10                  15

Asp Val Asn Tyr Glu Pro Asp Leu Asp Phe His Gln Gly Arg Leu Tyr
                20                  25                  30

Trp Ser Asp Leu Gln Ala Met Phe Leu Gln Phe Leu Gly Glu Gly Arg
            35                  40                  45

Leu Glu Asp Thr Ile Arg Gln Thr Ser Leu Arg Glu Arg Val Ala Gly
        50                  55                  60

Ser Ala Gly Met Ala Ala Leu Thr Gln Asp Ile Arg Ala Ala Leu Ser
65                  70                  75                  80

Arg Gln Lys Leu Asp His Val Trp Thr Asp Thr His Tyr Val Gly Leu
                85                  90                  95

Gln Phe Pro Asp Pro Ala His Pro Asn Thr Leu His Trp Val Asp Glu
                100                 105                 110

Ala Gly Lys Val Gly Glu Gln Leu Pro Leu Glu Asp Pro Asp Val Tyr
```

-continued

```
            115                 120                 125
Cys Pro Tyr Ser Ala Ile Gly Asn Val Thr Gly Glu Leu Val Tyr Ala
130                 135                 140
His Tyr Gly Arg Pro Glu Asp Leu Gln Asp Leu Arg Ala Arg Gly Val
145                 150                 155                 160
Asp Pro Val Gly Arg Leu Leu Val Arg Val Gly Val Ile Ser Phe
                165                 170                 175
Ala Gln Lys Val Thr Asn Ala Gln Asp Phe Gly Ala Gln Gly Val Leu
                180                 185                 190
Ile Tyr Pro Glu Pro Ala Asp Phe Ser Gln Asp Pro Pro Lys Pro Ser
                195                 200                 205
Leu Ser Ser Gln Gln Ala Val Tyr Gly His Val His Leu Gly Thr Gly
210                 215                 220
Asp Pro Tyr Thr Pro Gly Phe Pro Ser Phe Asn Gln Thr Gln Phe Pro
225                 230                 235                 240
Pro Val Ala Ser Ser Gly Leu Pro Ser Ile Pro Ala Gln Pro Ile Ser
                245                 250                 255
Ala Asp Ile Ala Ser Arg Leu Leu Arg Lys Leu Lys Gly Pro Val Ala
                260                 265                 270
Pro Gln Glu Trp Gln Gly Ser Leu Leu Gly Ser Pro Tyr His Leu Gly
                275                 280                 285
Pro Gly Pro Arg Leu Arg Leu Val Val Asn Asn His Arg Thr Ser Thr
                290                 295                 300
Pro Ile Asn Asn Ile Phe Gly Cys Ile Glu Gly Arg Ser Glu Pro Asp
305                 310                 315                 320
His Tyr Val Val Ile Gly Ala Gln Arg Asp Ala Trp Gly Pro Gly Ala
                325                 330                 335
Ala Lys Ser Ala Val Gly Thr Ala Ile Leu Leu Glu Leu Val Arg Thr
                340                 345                 350
Phe Ser Ser Met Val Ser Asn Gly Phe Arg Pro Arg Arg Ser Leu Leu
                355                 360                 365
Phe Ile Ser Trp Asp Gly Gly Asp Phe Gly Ser Val Gly Ser Thr Glu
                370                 375                 380
Trp Leu Glu Gly Tyr Leu Ser Val Leu His Leu Lys Ala Val Val Tyr
385                 390                 395                 400
Val Ser Leu Asp Asn Ala Val Leu Gly Asp Asp Lys Phe His Ala Lys
                405                 410                 415
Thr Ser Pro Leu Leu Thr Ser Leu Ile Glu Ser Val Leu Lys Gln Val
                420                 425                 430
Asp Ser Pro Asn His Ser Gly Gln Thr Leu Tyr Glu Gln Val Val Phe
                435                 440                 445
Thr Asn Pro Ser Trp Asp Ala Glu Val Ile Arg Pro Leu Pro Met Asp
                450                 455                 460
Ser Ser Ala Tyr Ser Phe Thr Ala Phe Val Gly Val Pro Ala Val Glu
465                 470                 475                 480
Phe Ser Phe Met Glu Asp Asp Gln Ala Tyr Pro Phe Leu His Thr Lys
                485                 490                 495
Glu Asp Thr Tyr Glu Asn Leu His Lys Val Leu Gln Gly Arg Leu Pro
                500                 505                 510
Ala Val Ala Gln Ala Val Ala Gln Leu Ala Gly Gln Leu Leu Ile Arg
                515                 520                 525
Leu Ser His Asp Arg Leu Leu Pro Leu Asp Phe Gly Arg Tyr Gly Asp
                530                 535                 540
```

```
Val Val Leu Arg His Ile Gly Asn Leu Asn Glu Phe Ser Gly Asp Leu
545                 550                 555                 560

Lys Ala Arg Gly Leu Thr Leu Gln Trp Val Tyr Ser Ala Arg Gly Asp
                565                 570                 575

Tyr Ile Arg Ala Ala Glu Lys Leu Arg Gln Glu Ile Tyr Ser Ser Glu
            580                 585                 590

Glu Arg Asp Glu Arg Leu Thr Arg Met Tyr Asn Val Arg Ile Met Arg
        595                 600                 605

Val Glu Phe Tyr Phe Leu Ser Gln Tyr Val Ser Pro Ala Asp Ser Pro
    610                 615                 620

Phe Arg His Ile Phe Met Gly Arg Gly Asp His Thr Leu Gly Ala Leu
625                 630                 635                 640

Leu Asp His Leu Arg Leu Leu Arg Ser Asn Ser Ser Gly Thr Pro Gly
                645                 650                 655

Ala Thr Ser Ser Thr Gly Phe Gln Glu Ser Arg Phe Arg Arg Gln Leu
            660                 665                 670

Ala Leu Leu Thr Trp Thr Leu Gln Gly Ala Ala Asn Ala Leu Ser Gly
        675                 680                 685

Asp Val Trp Asn Ile Asp Asn Asn Phe
    690                 695

<210> SEQ ID NO 2
<211> LENGTH: 696
<212> TYPE: PRT
<213> ORGANISM: Mus musculus

<400> SEQUENCE: 2

Arg Gly Ser Cys Gln Ala Cys Gly Asp Ser Val Leu Val Val Asp Glu
1               5                   10                  15

Asp Val Asn Pro Glu Asp Ser Gly Arg Thr Thr Leu Tyr Trp Ser Asp
            20                  25                  30

Leu Gln Ala Met Phe Leu Arg Phe Leu Gly Gly Arg Met Glu Asp
        35                  40                  45

Thr Ile Arg Leu Thr Ser Leu Arg Glu Arg Val Ala Gly Ser Ala Arg
50                  55                  60

Met Ala Thr Leu Val Gln Asp Ile Leu Asp Lys Leu Ser Arg Gln Lys
65                  70                  75                  80

Leu Asp His Val Trp Thr Asp Thr His Tyr Val Gly Leu Gln Phe Pro
                85                  90                  95

Asp Pro Ala His Ala Asn Thr Leu His Trp Val Asp Ala Asp Gly Ser
            100                 105                 110

Val Gln Glu Gln Leu Pro Leu Glu Asp Pro Glu Val Tyr Cys Pro Tyr
        115                 120                 125

Ser Ala Thr Gly Asn Ala Thr Gly Lys Leu Val Tyr Ala His Tyr Gly
    130                 135                 140

Arg Ser Glu Asp Leu Gln Asp Leu Lys Ala Lys Gly Val Glu Leu Ala
145                 150                 155                 160

Gly Ser Leu Leu Leu Val Arg Val Gly Ile Thr Ser Phe Ala Gln Lys
                165                 170                 175

Val Ala Val Ala Gln Asp Phe Gly Ala Gln Gly Val Leu Ile Tyr Pro
            180                 185                 190

Asp Pro Ser Asp Phe Ser Gln Asp Pro His Lys Pro Gly Leu Ser Ser
        195                 200                 205

His Gln Ala Val Tyr Gly His Val His Leu Gly Thr Gly Asp Pro Tyr
```

```
              210                 215                 220
Thr Pro Gly Phe Pro Ser Phe Asn Gln Thr Gln Phe Pro Pro Val Glu
225                 230                 235                 240

Ser Ser Gly Leu Pro Ser Ile Pro Ala Gln Pro Ile Ser Ala Asp Ile
                    245                 250                 255

Ala Asp Gln Leu Leu Arg Lys Leu Thr Gly Pro Val Ala Pro Gln Glu
                260                 265                 270

Trp Lys Gly His Leu Ser Gly Ser Pro Tyr Arg Leu Gly Pro Gly Pro
                275                 280                 285

Asp Leu Arg Leu Val Val Asn Asn His Arg Val Ser Thr Pro Ile Ser
            290                 295                 300

Asn Ile Phe Ala Cys Ile Glu Gly Phe Ala Glu Pro Asp His Tyr Val
305                 310                 315                 320

Val Ile Gly Ala Gln Arg Asp Ala Trp Gly Pro Gly Ala Ala Lys Ser
                    325                 330                 335

Ala Val Gly Thr Ala Ile Leu Leu Glu Leu Val Arg Thr Phe Ser Ser
                340                 345                 350

Met Val Ser Asn Gly Phe Arg Pro Arg Arg Ser Leu Leu Phe Ile Ser
                355                 360                 365

Trp Asp Gly Gly Asp Phe Gly Ser Val Gly Ala Thr Glu Trp Leu Glu
370                 375                 380

Gly Tyr Leu Ser Val Leu His Leu Lys Ala Val Val Tyr Val Ser Leu
385                 390                 395                 400

Asp Asn Ser Val Leu Gly Asp Gly Lys Phe His Ala Lys Thr Ser Pro
                405                 410                 415

Leu Leu Val Ser Leu Ile Glu Asn Ile Leu Lys Gln Val Asp Ser Pro
                420                 425                 430

Asn His Ser Gly Gln Thr Leu Tyr Glu Gln Val Ala Leu Thr His Pro
            435                 440                 445

Ser Trp Asp Ala Glu Val Ile Gln Pro Leu Pro Met Asp Ser Ser Ala
        450                 455                 460

Tyr Ser Phe Thr Ala Phe Ala Gly Val Pro Ala Val Glu Phe Ser Phe
465                 470                 475                 480

Met Glu Asp Asp Arg Val Tyr Pro Phe Leu His Thr Lys Glu Asp Thr
                485                 490                 495

Tyr Glu Asn Leu His Lys Met Leu Arg Gly Arg Leu Pro Ala Val Val
                500                 505                 510

Gln Ala Val Ala Gln Leu Ala Gly Gln Leu Leu Ile Arg Leu Ser His
                515                 520                 525

Asp His Leu Leu Pro Leu Asp Phe Gly Arg Tyr Gly Asp Val Val Leu
        530                 535                 540

Arg His Ile Gly Asn Leu Asn Glu Phe Ser Gly Asp Leu Lys Glu Arg
545                 550                 555                 560

Gly Leu Thr Leu Gln Trp Val Tyr Ser Ala Arg Gly Asp Tyr Ile Arg
                565                 570                 575

Ala Ala Glu Lys Leu Arg Lys Glu Ile Tyr Ser Ser Glu Arg Asn Asp
                580                 585                 590

Glu Arg Leu Met Arg Met Tyr Asn Val Arg Ile Met Arg Val Glu Phe
            595                 600                 605

Tyr Phe Leu Ser Gln Tyr Val Ser Pro Ala Asp Ser Pro Phe Arg His
        610                 615                 620

Ile Phe Leu Gly Gln Gly Asp His Thr Leu Gly Ala Leu Val Asp His
625                 630                 635                 640
```

Leu Arg Met Leu Arg Ala Asp Gly Ser Gly Ala Ala Ser Ser Arg Leu
              645                 650                 655

Thr Ala Gly Leu Gly Phe Gln Glu Ser Arg Phe Arg Arg Gln Leu Ala
              660                 665                 670

Leu Leu Thr Trp Thr Leu Gln Gly Ala Ala Asn Ala Leu Ser Gly Asp
              675                 680                 685

Val Trp Asn Ile Asp Asn Asn Phe
              690                 695

<210> SEQ ID NO 3
<211> LENGTH: 801
<212> TYPE: PRT
<213> ORGANISM: Homo sapiens

<400> SEQUENCE: 3

Met Glu Arg Leu Trp Gly Leu Phe Gln Arg Ala Gln Gln Leu Ser Pro
1               5                   10                  15

Arg Ser Ser Gln Thr Val Tyr Gln Arg Val Glu Gly Pro Arg Lys Gly
                20                  25                  30

His Leu Glu Glu Glu Glu Asp Gly Glu Glu Gly Ala Glu Thr Leu
            35                  40                  45

Ala His Phe Cys Pro Met Glu Leu Arg Gly Pro Glu Pro Leu Gly Ser
        50                  55                  60

Arg Pro Arg Gln Pro Asn Leu Ile Pro Trp Ala Ala Gly Arg Arg
65                  70                  75                  80

Ala Ala Pro Tyr Leu Val Leu Thr Ala Leu Leu Ile Phe Thr Gly Ala
                85                  90                  95

Phe Leu Leu Gly Tyr Val Ala Phe Arg Gly Ser Cys Gln Ala Cys Gly
                100                 105                 110

Asp Ser Val Leu Val Val Ser Glu Asp Val Asn Tyr Glu Pro Asp Leu
            115                 120                 125

Asp Phe His Gln Gly Arg Leu Tyr Trp Ser Asp Leu Gln Ala Met Phe
        130                 135                 140

Leu Gln Phe Leu Gly Glu Gly Arg Leu Glu Asp Thr Ile Arg Gln Thr
145                 150                 155                 160

Ser Leu Arg Glu Arg Val Ala Gly Ser Ala Gly Met Ala Ala Leu Thr
                165                 170                 175

Gln Asp Ile Arg Ala Ala Leu Ser Arg Gln Lys Leu Asp His Val Trp
            180                 185                 190

Thr Asp Thr His Tyr Val Gly Leu Gln Phe Pro Asp Pro Ala His Pro
        195                 200                 205

Asn Thr Leu His Trp Val Asp Glu Ala Gly Lys Val Gly Glu Gln Leu
    210                 215                 220

Pro Leu Glu Asp Pro Asp Val Tyr Cys Pro Tyr Ser Ala Ile Gly Asn
225                 230                 235                 240

Val Thr Gly Glu Leu Val Tyr Ala His Tyr Gly Arg Pro Glu Asp Leu
                245                 250                 255

Gln Asp Leu Arg Ala Arg Gly Val Asp Pro Val Gly Arg Leu Leu Leu
            260                 265                 270

Val Arg Val Gly Val Ile Ser Phe Ala Gln Lys Val Thr Asn Ala Gln
        275                 280                 285

Asp Phe Gly Ala Gln Gly Val Leu Ile Tyr Pro Glu Pro Ala Asp Phe
    290                 295                 300

Ser Gln Asp Pro Pro Lys Pro Ser Leu Ser Ser Gln Gln Ala Val Tyr

```
            305                 310                 315                 320
Gly His Val His Leu Gly Thr Gly Asp Pro Tyr Thr Pro Gly Phe Pro
                    325                 330                 335
Ser Phe Asn Gln Thr Gln Phe Pro Pro Val Ala Ser Ser Gly Leu Pro
                    340                 345                 350
Ser Ile Pro Ala Gln Pro Ile Ser Ala Asp Ile Ala Ser Arg Leu Leu
                    355                 360                 365
Arg Lys Leu Lys Gly Pro Val Ala Pro Gln Glu Trp Gln Gly Ser Leu
            370                 375                 380
Leu Gly Ser Pro Tyr His Leu Gly Pro Gly Pro Arg Leu Arg Leu Val
385                 390                 395                 400
Val Asn Asn His Arg Thr Ser Thr Pro Ile Asn Asn Ile Phe Gly Cys
                    405                 410                 415
Ile Glu Gly Arg Ser Glu Pro Asp His Tyr Val Val Ile Gly Ala Gln
                    420                 425                 430
Arg Asp Ala Trp Gly Pro Gly Ala Ala Lys Ser Ala Val Gly Thr Ala
                    435                 440                 445
Ile Leu Leu Glu Leu Val Arg Thr Phe Ser Ser Met Val Ser Asn Gly
            450                 455                 460
Phe Arg Pro Arg Arg Ser Leu Leu Phe Ile Ser Trp Asp Gly Gly Asp
465                 470                 475                 480
Phe Gly Ser Val Gly Ser Thr Glu Trp Leu Glu Gly Tyr Leu Ser Val
                    485                 490                 495
Leu His Leu Lys Ala Val Val Tyr Val Ser Leu Asp Asn Ala Val Leu
                    500                 505                 510
Gly Asp Asp Lys Phe His Ala Lys Thr Ser Pro Leu Leu Thr Ser Leu
            515                 520                 525
Ile Glu Ser Val Leu Lys Gln Val Asp Ser Pro Asn His Ser Gly Gln
            530                 535                 540
Thr Leu Tyr Glu Gln Val Val Phe Thr Asn Pro Ser Trp Asp Ala Glu
545                 550                 555                 560
Val Ile Arg Pro Leu Pro Met Asp Ser Ser Ala Tyr Ser Phe Thr Ala
                    565                 570                 575
Phe Val Gly Val Pro Ala Val Glu Phe Ser Phe Met Glu Asp Asp Gln
                    580                 585                 590
Ala Tyr Pro Phe Leu His Thr Lys Glu Asp Thr Tyr Glu Asn Leu His
                    595                 600                 605
Lys Val Leu Gln Gly Arg Leu Pro Ala Val Ala Gln Ala Val Ala Gln
            610                 615                 620
Leu Ala Gly Gln Leu Leu Ile Arg Leu Ser His Asp Arg Leu Leu Pro
625                 630                 635                 640
Leu Asp Phe Gly Arg Tyr Gly Asp Val Val Leu Arg His Ile Gly Asn
                    645                 650                 655
Leu Asn Glu Phe Ser Gly Asp Leu Lys Ala Arg Gly Leu Thr Leu Gln
                    660                 665                 670
Trp Val Tyr Ser Ala Arg Gly Asp Tyr Ile Arg Ala Ala Glu Lys Leu
            675                 680                 685
Arg Gln Glu Ile Tyr Ser Ser Glu Glu Arg Asp Glu Arg Leu Thr Arg
            690                 695                 700
Met Tyr Asn Val Arg Ile Met Arg Val Glu Phe Tyr Phe Leu Ser Gln
705                 710                 715                 720
Tyr Val Ser Pro Ala Asp Ser Pro Phe Arg His Ile Phe Met Gly Arg
                    725                 730                 735
```

```
Gly Asp His Thr Leu Gly Ala Leu Leu Asp His Leu Arg Leu Arg
            740                 745                 750

Ser Asn Ser Ser Gly Thr Pro Gly Ala Thr Ser Ser Thr Gly Phe Gln
            755                 760                 765

Glu Ser Arg Phe Arg Arg Gln Leu Ala Leu Leu Thr Trp Thr Leu Gln
770                 775                 780

Gly Ala Ala Asn Ala Leu Ser Gly Asp Val Trp Asn Ile Asp Asn Asn
785                 790                 795                 800

Phe
```

```
<210> SEQ ID NO 4
<211> LENGTH: 798
<212> TYPE: PRT
<213> ORGANISM: Mus musculus

<400> SEQUENCE: 4

Met Glu Gln Arg Trp Gly Leu Arg Arg Val Gln Gln Trp Ser Pro
1                   5                   10                  15

Arg Pro Ser Gln Thr Ile Tyr Arg Arg Val Glu Gly Pro Gln Leu Glu
            20                  25                  30

His Leu Glu Glu Glu Asp Arg Glu Glu Gly Ala Glu Leu Pro Ala Gln
            35                  40                  45

Phe Cys Pro Met Glu Leu Lys Gly Pro Glu His Leu Gly Ser Cys Pro
50                  55                  60

Gly Arg Ser Ile Pro Ile Pro Trp Ala Ala Gly Arg Lys Ala Ala
65                  70                  75                  80

Pro Tyr Leu Val Leu Ile Thr Leu Leu Ile Phe Thr Gly Ala Phe Leu
                85                  90                  95

Leu Gly Tyr Val Ala Phe Arg Gly Ser Cys Gln Ala Cys Gly Asp Ser
            100                 105                 110

Val Leu Val Val Asp Glu Asp Val Asn Pro Glu Asp Ser Gly Arg Thr
            115                 120                 125

Thr Leu Tyr Trp Ser Asp Leu Gln Ala Met Phe Leu Arg Phe Leu Gly
130                 135                 140

Glu Gly Arg Met Glu Asp Thr Ile Arg Leu Thr Ser Leu Arg Glu Arg
145                 150                 155                 160

Val Ala Gly Ser Ala Arg Met Ala Thr Leu Val Gln Asp Ile Leu Asp
                165                 170                 175

Lys Leu Ser Arg Gln Lys Leu Asp His Val Trp Thr Asp Thr His Tyr
            180                 185                 190

Val Gly Leu Gln Phe Pro Asp Pro Ala His Ala Asn Thr Leu His Trp
            195                 200                 205

Val Asp Ala Asp Gly Ser Val Gln Glu Gln Leu Pro Leu Glu Asp Pro
210                 215                 220

Glu Val Tyr Cys Pro Tyr Ser Ala Thr Gly Asn Ala Thr Gly Lys Leu
225                 230                 235                 240

Val Tyr Ala His Tyr Gly Arg Ser Glu Asp Leu Gln Asp Leu Lys Ala
                245                 250                 255

Lys Gly Val Glu Leu Ala Gly Ser Leu Leu Val Arg Val Gly Ile
            260                 265                 270

Thr Ser Phe Ala Gln Lys Val Ala Val Ala Gln Asp Phe Gly Ala Gln
            275                 280                 285

Gly Val Leu Ile Tyr Pro Asp Pro Ser Asp Phe Ser Gln Asp Pro His
            290                 295                 300
```

```
Lys Pro Gly Leu Ser Ser His Gln Ala Val Tyr Gly His Val His Leu
305                 310                 315                 320

Gly Thr Gly Asp Pro Tyr Thr Pro Gly Phe Pro Ser Phe Asn Gln Thr
            325                 330                 335

Gln Phe Pro Pro Val Glu Ser Ser Gly Leu Pro Ser Ile Pro Ala Gln
            340                 345                 350

Pro Ile Ser Ala Asp Ile Ala Asp Gln Leu Leu Arg Lys Leu Thr Gly
            355                 360                 365

Pro Val Ala Pro Gln Glu Trp Lys Gly His Leu Ser Gly Ser Pro Tyr
370                 375                 380

Arg Leu Gly Pro Gly Pro Asp Leu Arg Leu Val Val Asn Asn His Arg
385                 390                 395                 400

Val Ser Thr Pro Ile Ser Asn Ile Phe Ala Cys Ile Glu Gly Phe Ala
            405                 410                 415

Glu Pro Asp His Tyr Val Val Ile Gly Ala Gln Arg Asp Ala Trp Gly
            420                 425                 430

Pro Gly Ala Ala Lys Ser Ala Val Gly Thr Ala Ile Leu Leu Glu Leu
            435                 440                 445

Val Arg Thr Phe Ser Ser Met Val Ser Asn Gly Phe Arg Pro Arg Arg
450                 455                 460

Ser Leu Leu Phe Ile Ser Trp Asp Gly Gly Asp Phe Gly Ser Val Gly
465                 470                 475                 480

Ala Thr Glu Trp Leu Glu Gly Tyr Leu Ser Val Leu His Leu Lys Ala
            485                 490                 495

Val Val Tyr Val Ser Leu Asp Asn Ser Val Leu Gly Asp Gly Lys Phe
            500                 505                 510

His Ala Lys Thr Ser Pro Leu Leu Val Ser Leu Ile Glu Asn Ile Leu
            515                 520                 525

Lys Gln Val Asp Ser Pro Asn His Ser Gly Gln Thr Leu Tyr Glu Gln
530                 535                 540

Val Ala Leu Thr His Pro Ser Trp Asp Ala Glu Val Ile Gln Pro Leu
545                 550                 555                 560

Pro Met Asp Ser Ser Ala Tyr Ser Phe Thr Ala Phe Ala Gly Val Pro
            565                 570                 575

Ala Val Glu Phe Ser Phe Met Glu Asp Asp Arg Val Tyr Pro Phe Leu
            580                 585                 590

His Thr Lys Glu Asp Thr Tyr Glu Asn Leu His Lys Met Leu Arg Gly
            595                 600                 605

Arg Leu Pro Ala Val Val Gln Ala Val Ala Gln Leu Ala Gly Gln Leu
            610                 615                 620

Leu Ile Arg Leu Ser His Asp His Leu Leu Pro Leu Asp Phe Gly Arg
625                 630                 635                 640

Tyr Gly Asp Val Val Leu Arg His Ile Gly Asn Leu Asn Glu Phe Ser
            645                 650                 655

Gly Asp Leu Lys Glu Arg Gly Leu Thr Leu Gln Trp Val Tyr Ser Ala
            660                 665                 670

Arg Gly Asp Tyr Ile Arg Ala Ala Glu Lys Leu Arg Lys Glu Ile Tyr
            675                 680                 685

Ser Ser Glu Arg Asn Asp Glu Arg Leu Met Arg Met Tyr Asn Val Arg
            690                 695                 700

Ile Met Arg Val Glu Phe Tyr Phe Leu Ser Gln Tyr Val Ser Pro Ala
705                 710                 715                 720
```

```
Asp Ser Pro Phe Arg His Ile Phe Leu Gly Gln Gly Asp His Thr Leu
                725                 730                 735

Gly Ala Leu Val Asp His Leu Arg Met Leu Arg Ala Asp Gly Ser Gly
            740                 745                 750

Ala Ala Ser Ser Arg Leu Thr Ala Gly Leu Gly Phe Gln Glu Ser Arg
        755                 760                 765

Phe Arg Arg Gln Leu Ala Leu Leu Thr Trp Thr Leu Gln Gly Ala Ala
    770                 775                 780

Asn Ala Leu Ser Gly Asp Val Trp Asn Ile Asp Asn Asn Phe
785                 790                 795

<210> SEQ ID NO 5
<211> LENGTH: 94
<212> TYPE: PRT
<213> ORGANISM: Homo sapiens

<400> SEQUENCE: 5

Tyr Cys Pro Tyr Ser Ala Ile Gly Asn Val Thr Gly Glu Leu Val Tyr
1               5                   10                  15

Ala His Tyr Gly Arg Pro Glu Asp Leu Gln Asp Leu Arg Ala Arg Gly
            20                  25                  30

Val Asp Pro Val Gly Arg Leu Leu Val Arg Val Gly Val Ile Ser
        35                  40                  45

Phe Ala Gln Lys Val Thr Asn Ala Gln Asp Phe Gly Ala Gln Gly Val
    50                  55                  60

Leu Ile Tyr Pro Glu Pro Ala Asp Phe Ser Gln Asp Pro Pro Lys Pro
65                  70                  75                  80

Ser Leu Ser Ser Gln Gln Ala Val Tyr Gly His Val His Leu
                85                  90

<210> SEQ ID NO 6
<211> LENGTH: 186
<212> TYPE: PRT
<213> ORGANISM: Homo sapiens

<400> SEQUENCE: 6

Gly Arg Ser Glu Pro Asp His Tyr Val Val Ile Gly Ala Gln Arg Asp
1               5                   10                  15

Ala Trp Gly Pro Gly Ala Ala Lys Ser Ala Val Gly Thr Ala Ile Leu
            20                  25                  30

Leu Glu Leu Val Arg Thr Phe Ser Ser Met Val Ser Asn Gly Phe Arg
        35                  40                  45

Pro Arg Arg Ser Leu Leu Phe Ile Ser Trp Asp Gly Gly Asp Phe Gly
    50                  55                  60

Ser Val Gly Ser Thr Glu Trp Leu Glu Gly Tyr Leu Ser Val Leu His
65                  70                  75                  80

Leu Lys Ala Val Val Tyr Val Ser Leu Asp Asn Ala Val Leu Gly Asp
                85                  90                  95

Asp Lys Phe His Ala Lys Thr Ser Pro Leu Leu Thr Ser Leu Ile Glu
            100                 105                 110

Ser Val Leu Lys Gln Val Asp Ser Pro Asn His Ser Gly Gln Thr Leu
        115                 120                 125

Tyr Glu Gln Val Val Phe Thr Asn Pro Ser Trp Asp Ala Glu Val Ile
    130                 135                 140

Arg Pro Leu Pro Met Asp Ser Ser Ala Tyr Ser Phe Thr Ala Phe Val
145                 150                 155                 160
```

Gly Val Pro Ala Val Glu Phe Ser Phe Met Glu Asp Asp Gln Ala Tyr
                165                 170                 175

Pro Phe Leu His Thr Lys Glu Asp Thr Tyr
        180                 185

<210> SEQ ID NO 7
<211> LENGTH: 126
<212> TYPE: PRT
<213> ORGANISM: Homo sapiens

<400> SEQUENCE: 7

Leu Lys Ala Arg Gly Leu Thr Leu Gln Trp Val Tyr Ser Ala Arg Gly
1               5                   10                  15

Asp Tyr Ile Arg Ala Ala Glu Lys Leu Arg Gln Glu Ile Tyr Ser Ser
            20                  25                  30

Glu Glu Arg Asp Glu Arg Leu Thr Arg Met Tyr Asn Val Arg Ile Met
        35                  40                  45

Arg Val Glu Phe Tyr Phe Leu Ser Gln Tyr Val Ser Pro Ala Asp Ser
    50                  55                  60

Pro Phe Arg His Ile Phe Met Gly Arg Gly Asp His Thr Leu Gly Ala
65                  70                  75                  80

Leu Leu Asp His Leu Arg Leu Leu Arg Ser Asn Ser Ser Gly Thr Pro
                85                  90                  95

Gly Ala Thr Ser Ser Thr Gly Phe Gln Glu Ser Arg Phe Arg Arg Gln
            100                 105                 110

Leu Ala Leu Leu Thr Trp Thr Leu Gln Gly Ala Ala Asn Ala
        115                 120                 125

<210> SEQ ID NO 8
<211> LENGTH: 2538
<212> TYPE: DNA
<213> ORGANISM: Homo sapiens

<400> SEQUENCE: 8
gttcgttgca acaaattgat gagcaatgct tttttataat gccaactttg tacaaaaaag      60
ttggcaccat ggagcggctt tggggtctat tccagagagc gcaacaactg tccccaagat     120
cctctcagac cgtctaccag cgtgtggaag gcccccggaa agggcacctg aggaggaag      180 aggaagacgg ggaggagggg gcggagacat tggcccactt ctgccccatg agctgagggg    240
gccctgagcc cctgggctct agacccaggc agccaaacct cattccctgg gcggcagcag    300
gacggagggc tgcccccctac ctggtcctga cggccctgct gatcttcact ggggccttcc   360
tactgggcta cgtcgccttc cgagggtcct gccaggcgtg cggagactct gtgttggtgg    420
tcagtgagga tgtcaactat gagcctgacc tggatttcca ccagggcaga ctctactgga    480
gcgacctcca ggccatgttc ctgcagttcc tgggggaggg gcgcctggag gacaccatca    540
ggcaaaccag ccttcgggaa cgggtggcag gctcggccgg gatggccgct ctgactcagg    600
acattcgcgc ggcgctctcc cgccagaagc tggaccacgt gtggaccgac acgcactacg    660
tggggctgca attccccggat ccggctcacc ccaacaccct gcactgggtc gatgaggccg   720
ggaaggtcgg agagcagctg ccgctggagg accctgacgt ctactgcccc tacagcgcca   780
tcggcaacgt cacgggagag ctggtgtacg cccactacgg gcggcccgaa gacctgcagg   840
acctgcgggc caggggcgtg gatcagtgg gccgcctgct gctggtgcgc gtgggggtga    900
tcagcttcgc ccagaaggtg accaatgctc aggacttcgg ggctcaagga gtgctctatat    960 acccagagcc agcggacttc tcccaggacc cacccaagcc aagcctgtcc agccagcagg  1020

| | | |
|---|---|---|
| cagtgtatgg acatgtgcac ctgggaactg agacccccta cacacctggc ttcccttcct | 1080 | |
| tcaatcaaac ccagttccct ccagttgcat catcaggcct cccagcatcc ccagcccagc | 1140 | |
| ccatcagtgc agacattgcc tcccgcctgc tgaggaagct caaaggccct gtggccccc | 1200 | |
| aagaatggca ggggagcctc ctaggctccc cttatcacct gggcccgggg ccacgacttc | 1260 | |
| ggctagtggt caacaatcac aggacctcca ccccccatcaa caacatcttc ggctgcatcg | 1320 | |
| aaggccgctc agagccagat cactacgttg tcatcggggc ccagagggat gcatggggcc | 1380 | |
| caggagcagc taaatccgct gtggggacgg ctatactcct ggagctggtg cggacctttt | 1440 | |
| cctccatggt gagcaacggc ttccggcccc gcagaagtct cctcttcatc agctgggacg | 1500 | |
| gtggtgactt tggaagcgtg ggctccacgg agtggctaga gggctacctc agcgtgctgc | 1560 | |
| acctcaaagc cgtagtgtac gtgagcctgg acaacgcagt gctgggggat gacaagtttc | 1620 | |
| atgccaagac cagccccctt ctgacaagtc tcattgagag tgtcctgaag caggtggatt | 1680 | |
| ctcccaacca cagtgggcag actctctatg aacaggtggt gttcaccaat cccagctggg | 1740 | |
| atgctgaggt gatccggccc ctacccatgg acagcagtgc ctattccttc acggcctttg | 1800 | |
| tgggagtccc tgccgtcgag ttctcctttta tggaggacga ccaggcctac ccattcctgc | 1860 | |
| acacaaagga ggacacttat gagaacctgc ataaggtgct gcaaggccgc ctgcccgccg | 1920 | |
| tggcccaggc cgtggcccag ctcgcagggc agctcctcat ccggctcagc cacgatcgcc | 1980 | |
| tgctgcccct cgacttcggc cgctacgggg acgtcgtcct caggcacatc gggaacctca | 2040 | |
| acgagttctc tggggacctc aaggcccgcg ggctgaccct gcagtgggtg tactcggcgc | 2100 | |
| gggggggacta catccgggcg gcggaaaagc tgcggccgga gatctacagc tcggaggaga | 2160 | |
| gagacgagcg actgacacgc atgtacaacg tgcgcataat gcgggtggag ttctacttcc | 2220 | |
| tttcccagta cgtgtcgcca gccgactccc cgttccgcca catcttcatg ggccgtggag | 2280 | |
| accacacgct gggcgccctg ctggaccacc tgccggctgct gcgctccaac agctccggga | 2340 | |
| ccccccgggc cacctcctcc actggcttcc aggagagccg tttccggcgt cagctagccc | 2400 | |
| tgctcacctg gacgctgcaa ggggcagcca atgcgcttag cggggatgtc tggaacattg | 2460 | |
| ataacaactt cttgccaact ttcttgtaca agttggcat tataagaaag cattgcttat | 2520 | |
| caatttgttg caacgaac | 2538 | |

<210> SEQ ID NO 9
<211> LENGTH: 3597
<212> TYPE: DNA
<213> ORGANISM: Mus musculus

<400> SEQUENCE: 9

| | | |
|---|---|---|
| gagtctcctg ggagcatggt ccaagaaacc cagagacctg ttgctgagct gaacttggct | 60 | |
| gctgtgtctt cccactcagg actcggcttt gacaggcacg aggcagggac tggggtactg | 120 | |
| gtgagcccct acctctcaga tctttctgga cctggctgca ggtcctggtg tcttcgtcgc | 180 | |
| ggcttggatt tcaaactgga ggagttcagg aggggggcaca agcatggagc aacgttgggg | 240 | |
| tctacttcgg agagtgcaac agtggtcccc aagaccctct cagaccatct acagacgcgt | 300 | |
| ggaaggcccct cagctggagc acctggagga ggaagacagg gaggaagggg cggagcttcc | 360 | |
| tgcccagttc tgcccccatgg aactcaaagg ccctgagcac ttaggctcct gtcccgggag | 420 | |
| gtcaattccc ataccctggg ctgcagcagg tcgaaaggct gccccctatc tggtcctgat | 480 | |
| caccctgcta atcttcactg gggccttcct cctaggctac gtggccttc gagggtcctg | 540 | |

```
ccaggcgtgt ggggactccg tgttggtggt cgatgaagat gtcaaccctg aggactccgg      600
ccggaccacg ttgtactgga gcgacctcca ggccatgttt ctccggttcc ttggggaggg      660
gcgcatggaa gacaccatca ggctgaccag cctccgggaa cgcgtggctg gctcagccag      720
aatggccacc ctggtccaag atatcctcga taagctctcg cgccagaagc tggaccacgt      780
gtggactgac acgcactacg tgggacttca gttcccagat ccggctcacg ctaacaccct      840
gcactgggtg gatgcagacg ggagcgtcca ggagcagcta ccgctggagg atccggaagt      900
ctactgtccc tacagcgcca ccggcaacgc cacgggcaag ctggtgtacg cccactacgg      960
gcggtcggag gacctacagg acctaaaagc caagggcgtg gagctggccg cagcctcct      1020 gctagtgcga gttggaatta ctagcttcgc ccagaaggta gccgttgccc aggactttgg      1080
ggctcaagga gtgctgatat accctgaccc atcagacttc tcccaggatc cccacaagcc      1140
aggcctgtct agccaccagg ctgtgtacgg acatgtgcac ctgggaactg agaccctta      1200 cacacctggc ttcccgtcct tcaatcaaac ccagttccct ccagtagaat catcaggcct      1260
tcccagcatc cccgcccagc ccatcagtgc tgacattgct gatcaattgc tcaggaaact      1320
cacaggcccc gtggctcccc aggagtggaa aggtcacctc tcaggctctc cttatcggct      1380
gggacctggg cccgacttac gccttgtggt caacaaccac agagtctcta cccccatcag      1440
taacatcttt gcgtgcatcg agggcttttgc agagccagat cactatgttg tcattggggc      1500
ccagagggat gcatggggcc aggagcagca caagtctgca gtggggactg ccatcctgct      1560
ggagctggtt cggaccttct cttccatggt cagcaatggg ttcagacctc gaagaagtct      1620
tttgttcatc agctgggacg gaggtgactt tggcagcgtg ggagccacag agtggttgga      1680
gggctacctc agcgtgctac acctcaaagc tgttgtgtac gtgagcctgg acaactccgt      1740
gttgggagat ggcaaattcc atgctaagac cagccccctt ctcgtcagcc tcattgagaa      1800
tatcttgaag caggtggact cccctaacca tagtggacag accctctatg aacaagtggc      1860
actcaccacc cccagctggg atgctgaagt gattcagccc ctgcccatgg acagcagtgc      1920
atattccttc acagcctttg cggggtccc agctgtggag ttctccttca tggaggatga      1980
tcgggtgtac ccattcctgc acacgaagga ggacacatat gagaatctgc acaagatgct      2040
gcgaggtcgc ctgcccgccg tggtccaggc agtggctcag ctcgcgggcc agctcctcat      2100
ccgactgagc cacgatcacc tactgccgct agacttcggc cgctatggag acgtggttct      2160
caggcacatc ggcaacctca atgagttctc tggggacctc aaggagcgcg ggctgaccct      2220
gcagtgggtg tactctgcaa gggggacta catccgtgcg gcggaaaagc tgcggaagga      2280
gatttacagc tcggagcgga acgatgagcg tctgatgcgc atgtacaacg tgcgcatcat      2340
gagggtggag ttctacttcc tgtcccagta tgtgtcgcca gccgactccc cattccgcca      2400
cattttccta ggccaaggcg accacacttt gggtgccctg gtagaccacc tgcggatgct      2460
gcgcgccgat ggctcaggag ccgcctcttc ccggttgaca gcaggtctgg gcttccagga      2520
gagtcgcttc cggcgccagc tggcgctgct cacctgaca ctgcagggg cagccaacgc      2580 tctcagtggc gacgtttgga acattgacaa taacttttga agccaaaagc cctccatggg      2640
ccccacgtga ttctccttc tccctctttg agtggtgcag gcaaaggagg tgcctgagat      2700
tgtaacctat tcttaacacc cttggtcctg caatgctggt gcgccatatt ttctcagtgt      2760
ggttgtcatg ccgttgctta cccagaaagc ggttttcttc ccatcacagg cccttctgtc      2820
ttcaggagca aagttcccca tatctagaga ctatctagat gctgggatct gatcagctct      2880
cttagagagt gagatggaca gcgtcattat tttatgacac atgagctacg gtatgtgagc      2940
```

```
agcccaaggg gattagatgt caataaacca attgtaaccc ctgttgtcca tacgcaattt    3000
agcttcctct tcatgccgta cccactcctc atatccgcct tgagactagg gaagaaggca    3060
cagaaggcac ctgacagcat gcttgcaaga tgctatccac atgggaaaaa taactgttct    3120
gatgtctaag aaaactgcct aaagataatg gataggaggt ggggcagtgg ggataactca    3180
tcaggaatgg gtgattgcgg ccaagcctga tgacctgagt ttaatcccca ggaccaacat    3240
ggcaaaagga gagaactagt tcccacaagt tttcctatat cctccaaatg tatgcccata    3300
aaagcacaaa tagataaatg tttttgcttt tgtttttttaa agtggctttg tggttaagag    3360
cactggatgc cattctagaa gacaccggtt cgattcccag cacccacatg gccgcttaca    3420
actgtctgta actccagttg ctggggatca gatgccctct tctggtatgg tgtacgactg    3480
catgcatgta gtatacatac aagcaggcaa aatacccata catgtaaaat tttaaaaaa    3540 tagtttaaat tataaattaa tttaaagaac aaataaaaga ttaatgcctt taatccc      3597
```

USE OF THE EXTRACELLULAR DOMAIN OF TRANSFERRIN RECEPTOR 2 FOR THE DIAGNOSIS AND TREATMENT OF PRIMARY OR SECONDARY SCLEROSING DISEASES

CROSS REFERENCE TO RELATED APPLICATIONS

This application is a national stage application under 35 U.S.C. § 371 of International Application No. PCT/EP2018/065846, filed internationally on Jun. 14, 2018, which claims priority benefit to European Application No. 17176043.2, filed Jun. 14, 2017, the contents of which are incorporated herein by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 165062000200SEQLIST.TXT, date recorded: Dec. 11, 2019, size: 38,017 bytes).

DETAILED DESCRIPTION

The invention relates to a protein for use in diagnosing and treating primary or secondary sclerosing diseases, a fusion protein, and nucleotide sequence and a vector, and to a pharmaceutical composition for use in diagnosing and treating primary or secondary sclerosing diseases.

There are numerous sclerosing diseases that are associated with uncontrolled bone formation, including Fibrodysplasia ossificans progressiva (FOP). This rare disease is characterized by heterotopic ossification (HO) which leads to ossification outside of the skeleton, in particular of muscles, tendons and soft parts, and thus greatly impairs the mobility of patients. FOP sufferers have an average life expectancy of 56 years and the cause of death is often the inability of the thorax to support normal respiration. FOP patients have a mutation in the ACVR1-Gen, which codes for the ACVR1/ALK2 receptor. This receptor is part of the bone morphogenetic protein (BMP) signaling pathway and is of decisive importance in the regulation of cartilage and bone development. This mutation leads to increased activity of the ACVR1/ALK2 receptor and thus to excessive BMP signaling, resulting in increased and uncontrolled bone formation (Shore and Kaplan 2008).

Other sclerosing diseases exist, in addition to FOP, and result from different mechanisms. These include van Buchem disease, sclerosteosis, melorheostosis, pachydermoperiostosis, fibrous dysplasia, osteochondrodysplasia, mucopolysaccharidosis, ankylosing spondylitis, post-traumatic HO, e.g. after joint replacement operations, explosions, amputations, paraplegia, or after calciphylaxis or in the case of malign diseases or degenerative diseases, e.g. prostate carcinomas, renal cell carcinomas, tumoral calcinosis, breast carcinomas, arthrosis or benign bone lesions. These sclerosing diseases are characterized by uncontrolled ossification within and outside of the skeleton.

Conventional methods for treating sclerosing diseases comprise non-specific treatments, steroids, non-steroidal anti-inflammatory drugs (NSAIDs), resection or radiotherapy (Kölbl et al. 2003).

WO 2016/039796 A2 describes a method for treating the sclerosing disease Fibrodysplasia ossificans progressiva (FOP), comprising the administration of activin receptor type 2A (ACVR2A) antagonist and/or activin receptor type 2B (ACVR2B) antagonist or activin receptor type 1 ACVR1) antagonist.

However, the applications of these treatments are limited and usually only symptom-relieving, but cannot prevent the disease from progressing. For example, following resection, the likelihood of HO returning is up to 80%. Steroids in particular cause inhibition of bone formation but have a large number of side effects, such as obesity, diabetes, dry skin or muscle wasting.

WO 2015/107075 A1 discloses the human amino acid sequence of the extracellular domains of transferrin receptor 2 (SEQ ID NO. 1). Baschant et al. describe the iron-dependent, cell-intrinsic negative regulation of osteoclast formation using transferrin receptor 2 (Baschant et al. 2017).

The object of the present invention is therefore that of providing a drug for treating sclerosing diseases.

The object of the invention is furthermore that of providing a drug that has fewer side effects than known treatment methods.

The object is achieved according to the invention by the protein having an amino acid sequence that has at least 70% identity with the sequence of SEQ ID NO. 1, or the fragments thereof, for use in diagnosing and treating primary or secondary sclerosing diseases.

"Identity" is to be understood as the number of matching amino acids based on the total number of amino acids.

A "fragment" is to be understood as a portion of the amino acid sequence of the protein according to the invention, preferably a fragment consisting of the PA domains (SEQ ID NO. 5), a fragment consisting of the peptidase M28 domains (SEQ ID NO. 6), or a fragment consisting of the Tfr-like dimerization domains (SEQ ID NO. 7).

"Primary or secondary sclerosing diseases" are to be understood as diseases associated with ossification of tissue, the sclerosis occurring as a primary or secondary consequence of the disease.

Primary or secondary sclerosing diseases comprise Fibrodysplasia ossificans progressiva (FOP), van Buchem disease, sclerosteosis, melorheostosis, pachydermoperiostosis, fibrous dysplasia, osteochondrodysplasia, mucopolysaccharidosis, ankylosing spondylitis, post-traumatic HO, preferably in the case of scleroses after joint replacement operations, explosions, amputations, paraplegia, calciphylaxis or in the case of malign diseases or degenerative diseases, particularly preferably in the case of prostate carcinomas, renal cell carcinomas, tumoral calcinosis, breast carcinomas, arthrosis and benign bone lesions.

In a preferred embodiment, the use is in diagnosing and treating heterotopic ossification (HO), van Buchem disease, sclerosteosis or Fibrodysplasia ossificans progressiva (FOP).

"HO," also known as Myositis ossificans, is to be understood as a disease in which ossification of the soft part tissue outside of the skeletal system occurs as a result of tissue injury.

"Fibrodysplasia ossificans progressiva (FOP)," also known as Fibrodysplasia ossificans multiplex progressiva, Myositis ossificans progressiva or Munchmeyer's disease, is to be understood as a genetic disease in which progressive ossification of the connective and supporting tissue of the human body occurs.

"Van Buchem disease," also known as van Buchem syndrome, sclerosteosis, Hyperostosis corticalis generalisata familiaris, van Buchem-type endosteal hyperostosis is to be understood as a hereditary skeletal dysplasia comprising hyperplasia of the long bones and the skullcap, which disease is autosomal recessive.

"Fibrous dysplasia" is to be understood as a disease that is caused by a mutation in the GNAS gene and leads to bone excrescences.

"Melorheostosis" is to be understood as a disease that is caused by a mutation in the LEMD3 gene and leads to bone excrescences. This gene codes for a protein that is involved in the transforming growth factor-β (TGF-β) signaling pathway.

"Mucopolysaccharidosis" is to be understood as a group of lysosomal storage diseases that is autosomal recessive and leads to bone changes.

"Ankylosing spondylitis," Bechterew's disease, Marie-Strumpell disease, ankylosing spondyloarthritis is a chronic inflammatory disease that is preferably manifested in the spinal column and in the sacroiliac joint. In this case, ankylosis and stiffening often occurs in the spinal column.

The protein having an amino acid sequence SEQ ID NO. 1 can be isolated from the human transferrin receptor (Tfr) 2α, the human transferrin receptor (Tfr) 2β, preferably the extracellular domains of human Tfr2α.

The protein according to the invention preferably binds members of the transforming growth factor-β (TGF-β)/bone morphogenetic proteins BMP families, preferably BMPs, particularly preferably BMP-2, BMP-4, BMP-6 and BMP-7.

"Transforming growth factor-β (TGF-β)/bone morphogenetic protein, BMP families," is to be understood as a group of similar signaling proteins that bind members of the TGF-β receptor families. The TGF-β/BMP family comprises TGFβ1, TGFβ2, TGFβ3, BMPs, growth differentiation factors (GDFs), activin and inhibin, myostatin, anti-Müllerian hormone (AMH) and nodal.

"Bone morphogenetic proteins (BMPs)" are to be understood as a group of paracrine signaling proteins that bind BMP receptors. In an embodiment, BMPs are selected from BMP1, BMP2, BMP3, BMP4, BMP5, BMP6, BMP7, BMP8a, BMP8b, BMP-9, BMP10 or BMP15, preferably BMP-2, BMP-4, BMP-6 or BMP-7.

Advantageously, when treating primary or secondary sclerosing diseases using the protein according to the invention, the BMP signaling pathway, and thus the bone formation and the Wnt signaling pathway is specifically inhibited.

In an embodiment, the diagnosis of primary or secondary sclerosing diseases using the protein according to the invention is carried out by detecting members of the TGF-β/BMP family, preferably BMPs, particularly preferably BMP-2, BMP-4, BMP-6 and BMP-7.

In an embodiment, the diagnosis of primary or secondary sclerosing diseases using the protein according to the invention is carried out in the blood, in the blood plasma, in the blood serum or in the tissue. In a preferred embodiment, the tissue is bone or cartilage. "Blood plasma" is to be understood as the fluid component of the blood. "Blood serum" is to be understood as the blood plasma without the clotting factor.

In an embodiment, the diagnosis of primary or secondary sclerosing diseases using the protein according to the invention is carried out by means of an immunoassay. An "immunoassay" is to be understood as a detection procedure in which an analyte is detected in a fluid phase by means of antigen-antibody binding.

In an embodiment, the immunoassay is selected from an Enzyme-linked Immunosorbent Assay (ELISA) or Enzyme-linked Immuno Spot Assay (ELIspot Assay). An "ELISA" is to be understood as an antibody-based detection procedure that is based on an enzymatic color reaction. An "ELIspot Assay" is to be understood as a detection procedure for detecting antibodies that are secreted by immune cells following stimulation using antigens and are immobilized on a membrane.

In an embodiment, the diagnosis of primary or secondary sclerosing diseases is carried out in order to assess the prognosis of the disease, to assess the response to treatment and/or for risk stratification. "Risk stratification" is to be understood as assessing the risk of a disease progressing or leading to complications or death.

In an embodiment, the protein according to the invention for use in diagnosing and treating primary or secondary sclerosing diseases comprises sequence SEQ ID NO. 1 or SEQ ID NO. 2.

The protein having an amino acid sequence SEQ ID NO. 2 can be isolated from the murine transferrin receptor (Tfr) 2α, the murine transferrin receptor (Tfr) 2β, preferably the extracellular domains of murine Tfr2α.

In an embodiment, the protein according to the invention comprises 232 amino acids to 801 amino acids, preferably 487 amino acids to 801 amino acids, particularly preferably 600 amino acids to 750 amino acids.

In an embodiment, the protein according to the invention for use in diagnosing and treating primary or secondary sclerosing diseases is the human transferrin receptor (Tfr) 2α (SEQ ID NO. 3), the murine transferrin receptor (Tfr) 2α (SEQ ID NO. 4), the human transferrin receptor (Tfr) 2β (SEQ ID NO. 1) or the extracellular domains of human Tfr2α (SEQ ID NO. 1), the murine transferrin receptor (Tfr) 2β (SEQ ID NO. 2) or the extracellular domains of murine Tfr2α (SEQ ID NO. 2).

The invention further relates to a fusion protein comprising at least one protein according to the invention for use in diagnosing and treating primary or secondary sclerosing diseases.

In an embodiment, the fusion protein comprises at least one protein tag. In an embodiment, the at least one protein tag is selected from a polyhistidine (His) tag, glutathione S-transferase (GST) tag, maltose binding protein (MBP) tag, Myc tag, streptavidin (Strep) tag or a dye, preferably a fluorescent dye, particularly preferably a green fluorescent protein (GFP) or a yellow fluorescent protein (YFP).

In an embodiment, the protein according to the invention or the fusion protein comprising at least one protein according to the invention comprises at least one modification.

In an embodiment, the at least one modification is selected from proteins containing D-amino acids, pseudopeptide bonds, amino alcohols, non-proteinogenic amino acids, amino acids having modified side groups and/or circular proteins.

Proteins comprising modifications are advantageously more stable.

In an embodiment, the protein according to the invention or the fusion protein comprising at least one protein according to the invention is used in the treatment of diseases associated with increased BMP receptor activation.

The invention further relates to a nucleotide sequence comprising a sequence coding for a protein according to the invention or a fusion protein comprising at least one protein according to the invention for use in diagnosing and treating primary or secondary sclerosing diseases.

In an embodiment, the nucleotide sequence comprises SEQ ID NO. 8 or SEQ ID NO. 9.

A further aspect of the invention relates to a vector for use in diagnosing and treating primary or secondary sclerosing diseases, comprising a nucleotide sequence comprising a sequence coding for a protein according to the invention or a fusion protein comprising at least one protein according to the invention.

A "vector" is to be understood as a nucleic acid carrier for transferring a nucleic acid into a cell by means of transfection or transduction. In an embodiment, vectors are selected from plasmids, viral vectors or other nucleic acid carriers that contain a nucleotide sequence comprising a sequence coding for a protein according to the invention or a fusion protein comprising at least one protein according to the invention by means of genetic recombination (recombinant).

The invention further relates to a pharmaceutical composition for use in treating primary or secondary sclerosing diseases, comprising at least one protein according to the invention or a fusion protein comprising at least one protein according to the invention.

In an embodiment, the pharmaceutical composition is a solution, tablet or capsule. In an embodiment, the protein according to the invention is used as a coating for implant materials, preferably metals or plastics materials, and/or implants, preferably prostheses, screws or nails.

In an embodiment, the pharmaceutical composition is administered locally in an intraarticular or intramuscular manner, or systemically in a subcutaneous or intravenous manner, or by means of oral administration. In an embodiment, the pharmaceutical composition is in a suitable form for intraarticular, intramuscular, subcutaneous, intravenous or oral administration.

In an embodiment, the pharmaceutical composition contains the protein according to the invention or the fusion protein comprising at least one protein according to the invention in a dose of from 10 µg/kg to 100 mg/kg body weight per administration.

In a further embodiment, the pharmaceutical composition furthermore contains a pharmaceutically acceptable diluent or base. In an embodiment, the pharmaceutically acceptable diluent or base is an aqueous solution, preferably a buffered aqueous solution, an aqueous saline solution or an aqueous glycine solution. In an embodiment, the buffered aqueous solution is selected from a histidine-buffered aqueous solution having a pH of from pH 5.0 to pH 7.0, or a sodium succinate-, sodium citrate-, sodium phosphate-, or potassium phosphate-buffered aqueous solution. In an embodiment, the buffered aqueous solution has a concentration of from 1 mmol/l (mM) to 500 mM, preferably 1 mM to 50 mM. In a further embodiment, the pharmaceutically acceptable diluent or base comprises sodium chloride, preferably in a concentration of between 0 mM and 300 mM, particularly preferably in a concentration of 150 mM.

In an embodiment, the pharmaceutical composition furthermore comprises at least one pharmaceutically acceptable excipient. An "excipient" is understood to be a compound that adjusts physiological conditions with regard to the pH and/or the ionic strength, and/or increases the stability of the pharmaceutical composition. In an embodiment, the at least one pharmaceutically acceptable excipient is selected from sodium acetate, sodium chloride, potassium chloride, calcium chloride or sodium lactate.

In an embodiment, the pharmaceutical composition is sterile. The pharmaceutical composition is sterilized by means of known methods.

A further aspect of the invention relates to the use of the pharmaceutical composition in diagnosing and treating primary or secondary sclerosing diseases.

In an embodiment, the use of the pharmaceutical composition is for administration to a subject. A "subject" is to be understood as an individual or a patient. In an embodiment, the subject is selected from humans or animals. In an embodiment, are selected from rodents, preferably mice, rats, hamsters or guinea pigs; dogs, rabbits, farm animals, preferably goats, sheep, pigs; and non-human primates, preferably chimpanzees, orangutans or gorillas.

In an embodiment, the pharmaceutical composition is used in diagnosing members of the TGF-β/BMP family and treating diseases associated with increased BMP receptor activation.

The invention further relates to a method for diagnosing and/or treating primary or secondary sclerosing diseases, comprising administering the protein according to the invention and/or the pharmaceutical composition.

In an embodiment, the diagnosis and/or treatment of primary or secondary sclerosing diseases is carried out on humans.

For the diagnosis and/or treatment, a sterile pharmaceutical composition, containing a pharmacologically active dose of one or more proteins according to the invention, is administered to a patient in order to diagnose and/or treat primary or secondary sclerosing diseases.

In an embodiment, the administration takes place locally, preferably as a intraarticular or intramuscular injection; or systemically, preferably as a subcutaneous, intramuscular or intravenous injection or infusion, or by means of oral or transdermal administration.

A further aspect of the invention relates to the use of the protein according to the invention or the fusion protein comprising at least one protein according to the invention in diagnosing members of the TGF-β/BMP family or in diagnosing diseases associated with increased BMP receptor activation.

"Increased BMP receptor activation" is to be understood as activation of at least one BMP receptor, which activation is brought about by a mutation of a BMP receptor (Shore and Kaplan 2008), preferably constitutively activating mutations. "Constitutively activating mutations" are to be understood as mutations in which at least one BMP receptor is activated in the absence of BMPs.

A further aspect of the invention relates to the use of a nucleotide sequence, comprising a sequence coding for a protein according to the invention or a fusion protein comprising at least one protein according to the invention, and/or of a vector, comprising a nucleotide sequence comprising a sequence coding for a protein according to the invention or a fusion protein comprising at least one protein according to the invention, in diagnosing members of the TGF-β/BMP family or in diagnosing diseases associated with increased BMP receptor activation.

In addition to the use in diagnosing and/or treating primary or secondary sclerosing diseases, the proteins according to the invention are suitable for biological research and other applications in which the detection of a member of the TGF-β/BMP family is of interest. Applications of this kind are in particular Western Blot, immunostaining of cells (e.g. for flow cytometry and microscopy) and ELISA, and the use as a tracer in imaging techniques such as CT (computer tomography), PET/CT (positron emission tomography).

In order to implement the invention, it is also expedient to combine the above embodiments and features of the claims.

EMBODIMENTS

The invention will be explained in greater detail in the following, with reference to some embodiments and accompanying drawings. In this case, the embodiments are intended to describe the invention but without having a limiting effect.

In the drawings:

FIG. 1: schematic depiction of the influence of BMPs (1) on bone formation (left-hand side). BMPs bind BMP receptors (BMPR-I (2) or BMPR-II (3)), triggering a signaling cascade (phosphorylation (8) of Smad protein (6) and MAP kinase (7)) which activates bone formation (10) by the expression of osteoblast genes (9). Schematic depiction of the binding of BMPs (1) to Tfr2α (4) (center). Schematic depiction of the influence of the protein (5) according to the invention on bone formation (10) (right-hand side). The proteins (5) according to the invention bind BMPs (1), as a result of which binding to BMP receptors (BMPR-I (2) or BMPR-II (3)) does not occur, and bone formation is not activated.

Figure 2A:
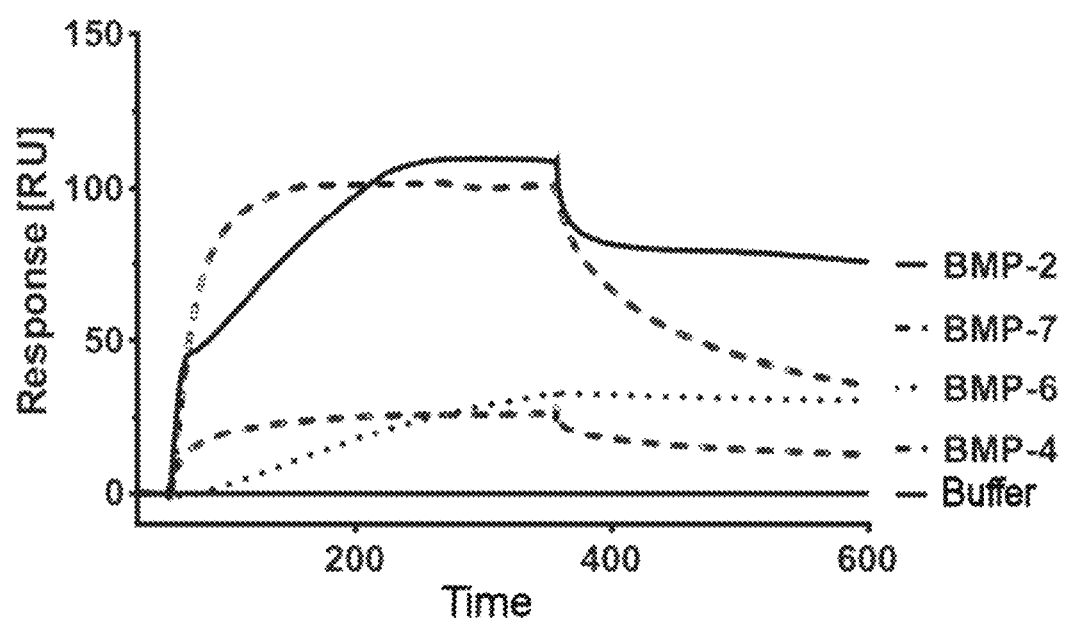
Figure 2B:
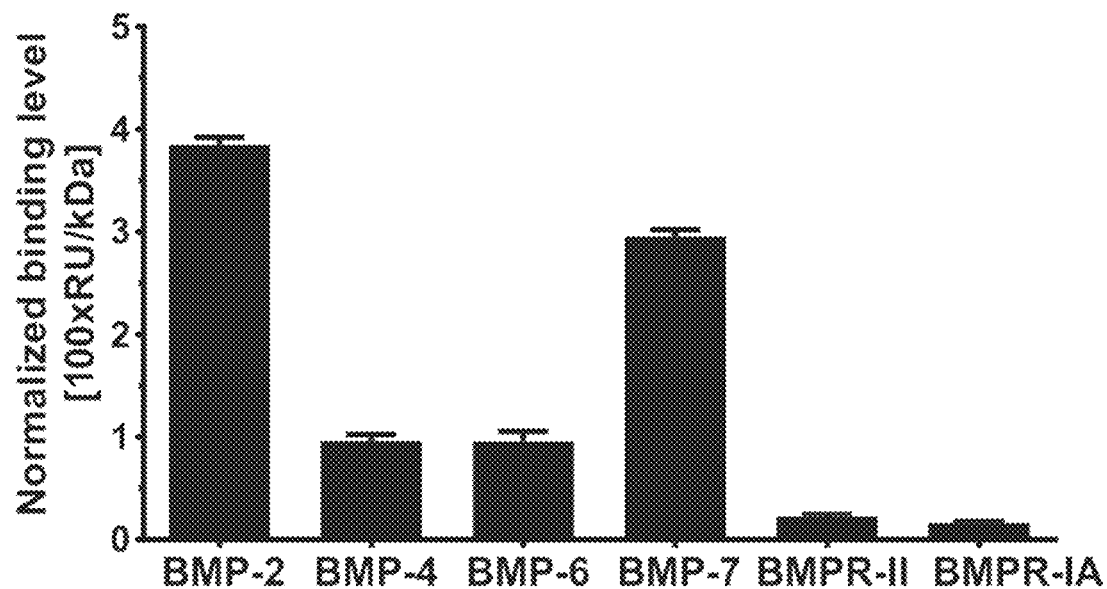

FIG. 2 shows SPR measurements of the binding of BMPs and the proteins according to the invention. FIG. 2A shows the binding of BMP-2, BMP-4, BMP-6 and BMP-7 to Tfr2-ECD. FIG. 2B shows a quantification of the binding level based on the molar mass of BMP-2, BMP-4, BMP-6 and BMP-7 to Tfr2-ECD compared with the binding level of BMPR-II and BMPR-IA.

Figure 3A:
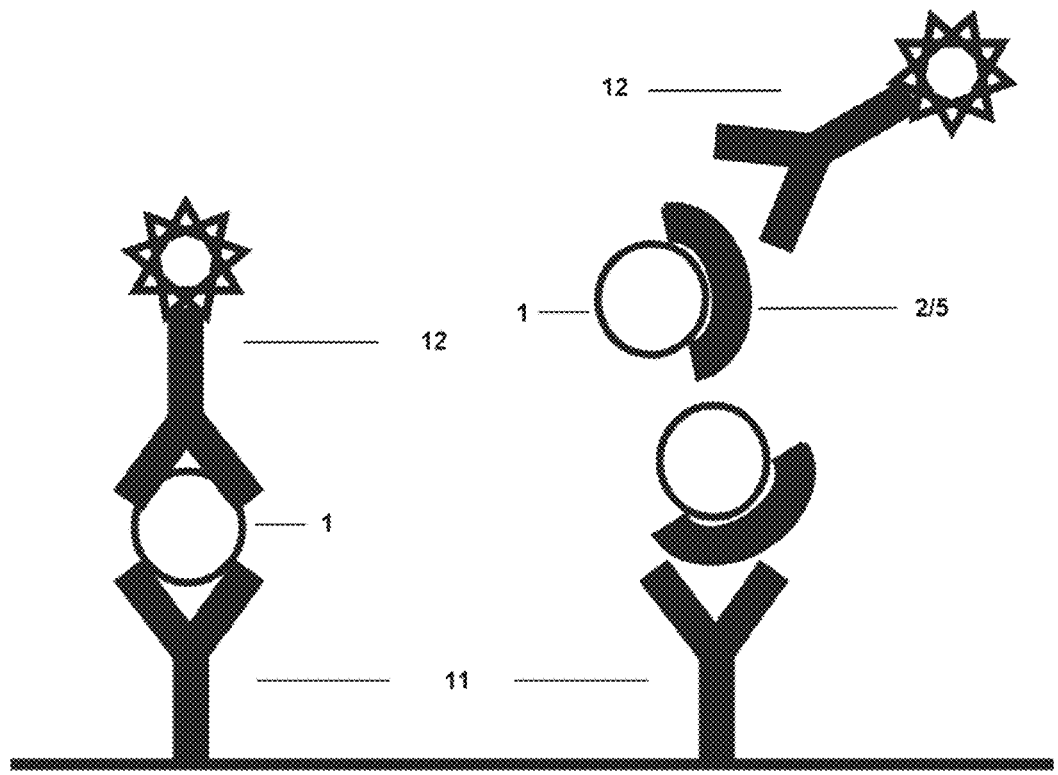
Figure 3B:
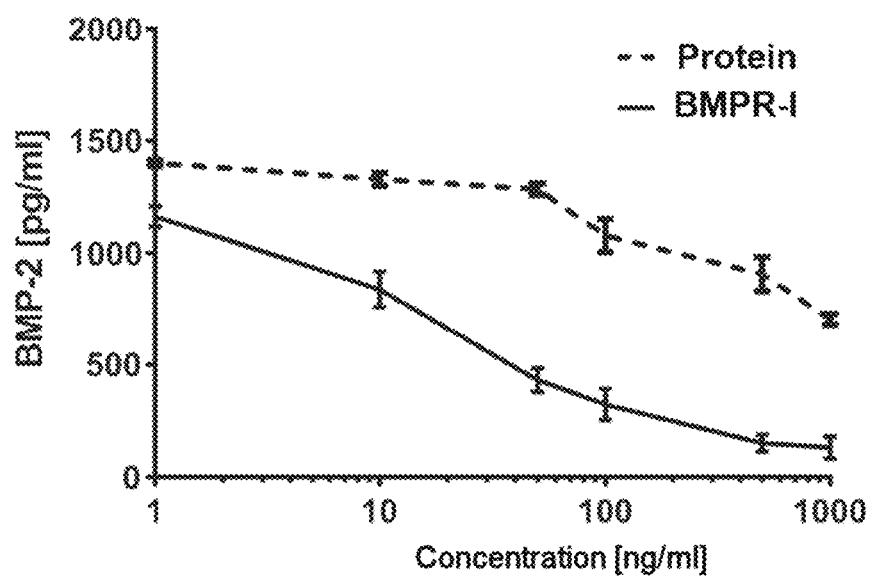

FIG. 3A schematically shows the BMP-2-competitive ELISA (enzyme linked immunosorbent assay): signal due to binding of BMPs (1), in particular BMP-2, to the capture antibody (11) and binding of the detection antibody (12) to BMP-2 (left-hand side). Reduced signal owing to the binding of the protein (5) according to the invention or BMPR-I (2) to BMP-2, as a result of which binding of the capture antibody (11) and detection antibody (12) does not occur (right-hand side). FIG. 3B: BMP-2-competitive ELISA: Influence of the concentration of the protein according to the invention or BMP-I on the signal of the BMP-2 detection antibody while the BMP-2 concentration remains unchanged.

Figure 4A:
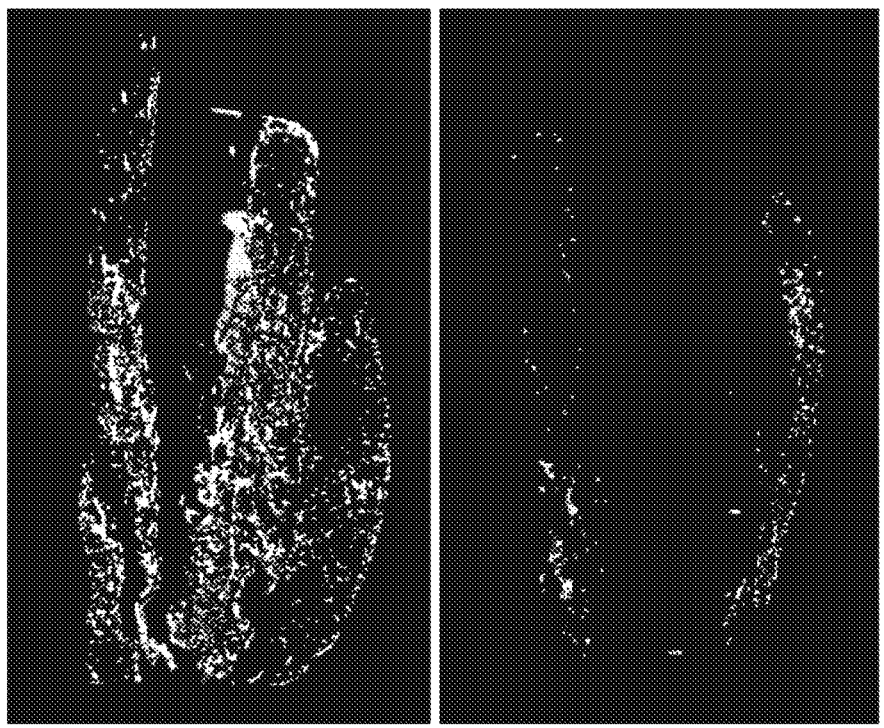
Figure 4B:
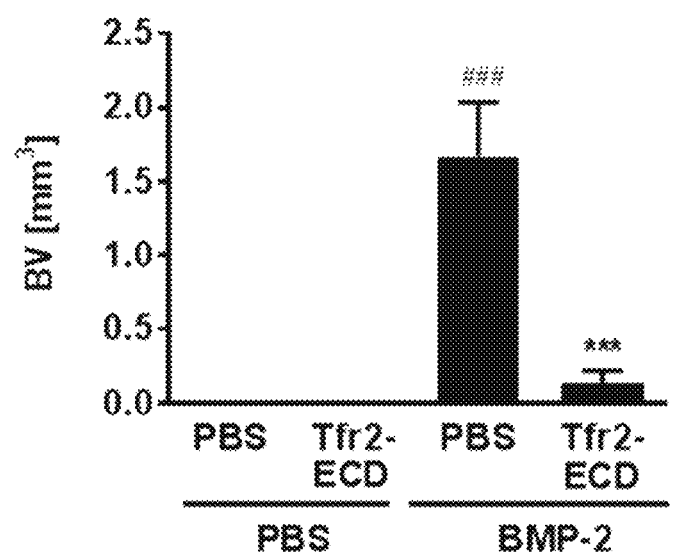

FIG. 4 shows the inhibition of HO in mice (C57BL/6 mice) using the protein according to the invention, in particular Tfr2-ECD, by means of binding of BMP-2. FIGS. 4A and 4B show the mineralization by determining the bone volume by means of μCT (microtomography). FIG. 4A shows the CT scans of the bone formation when BMP-2 is applied and when BMP-2 is applied together with Tfr2-ECD. FIG. 4B shows the quantification of the bone volume. PBS is used as a negative control. When BMP-2 is applied, the increase in the bone volume is evident after two weeks. Applying BMP-2 together with Tfr2-ECD exhibits a significant reduction in bone formation compared with BMP-2 as a reference (average value±standard deviation; n=3-6 per group; ***p<0.001 with respect to PBS (control).

PREPARATION OF THE TFR2 EXTRACELLULAR DOMAINS (TFR2-ECD)

The nucleic acid sequence of the entirety of the murine extracellular domains (ECD, aa 103-798) of Tfr2, including a 6× His tag, is carried out by Genscript (Germany). The recombinant His-Tfr2-ECD is expressed in Sf9 insect cells using the baculovirus expression system (pOCC211-Tfr2-ECD). Cell culture supernatants are collected and purified using a HisTrap column. After the step of washing using phosphate-buffered saline solution (PBS), the His-Tfr2-ECD-protein is eluted with imidazole by means of PBS.

Surface Plasmon Resonance Measurement (SPR)

The interactions between Tfr2-ECD and BMPs (BMP-2, -4, -6, -7 by R&D Systems) and BMP receptors (BMPR-IA, BMPR-II by R&D Systems) are analyzed using Biacore T100 (GE Healthcare).

For this purpose, Tfr2-ECD is immobilized on a Series S Sensor Chip C1 (GE Healthcare), by means of coupling the amino groups at 25° C. The carboxyl groups on the chip surface are activated for 7 minutes using a mixture of 196 mM 1-ethyl-3-(3-dimethylaminopropyl)-carbodiimide-hydrochloride and 50 mM n-hydroxysuccinimide at a flow rate of 10 μl/min. Subsequently, 5 μg/ml Tfr2-ECD, diluted with sodium acetate buffer (pH 4.5), is injected at a flow rate of 5 μl/min up to a relative occupancy of 200 RU. Non-reacted groups are inactivated by injecting 1 M thanolamine-HCl (pH 8.5) for 7 minutes at a flow rate of 10 μl/min. In order to prepare a reference surface, the same procedure is carried out but without Tfr2-ECD being injected.

The binding assays are carried out at 37° C. at a flow rate of 30 μl/min. Each analyte is diluted by a running buffer (HBS-P, pH 7.4 together with 50 nM $FeCl_3$). BMPs are used in a concentration of 50 nM and BMP receptors are used in a concentration of 200 nM. The binding assays are carried out by means of analyte injection for 300 s over the Tfr2-ECD surface, followed by dissociation for 1000 s. The values of the binding level are read out, relative to the baseline, 10 s before the end of the injection and are corrected with respect to the molar mass. Following the dissociation for 1000 s, the chip surface is regenerated for 60 s by means of HBS-P together with 5 M NaCl and 50 mM NaOH and is stabilized for 1000 s. The binding parameters are determined using the Biacore™ T100 evaluation software 2.03.

FIG. 2 shows the binding of the protein according to the invention to various BMP ligands (BMP-2, BMP-4, BMP-6, BMP-7).

BMP-2-Competitive ELISA (Enzyme Linked Immunosorbent Assay)

In order to carry out the BMP-2-competitive ELISA, the Duo Set BMP-2 ELISA kit by R&D Systems is used. After the plate has been coated, overnight, with BMP-2 capture antibodies, 1.5 ng/ml BMP-2 together with increasing concentrations of Tfr2-ECD or BMPR-IA (positive control, R&D Systems) is added to the assay. Following incubation for 1 hour at room temperature and intensive washing, the detection antibody is added according to the manufacturer's specifications and the amount of BMP-2 not bound to Tfr2-ECD or BMPR-IA that is bound to the capture and detection antibody is quantified.

FIG. 3 shows the binding of the protein according to the invention to BMPs, in particular BMP-2. As the concentration of the protein according to the invention increases, the signal of the BMP-2 detection antibody reduces, despite the BMP-2 concentration remaining the same. The progression is comparable to the binding of BMP-2 to the BMP receptor I (BMPR-I).

Mouse Model of Heterotopic Ossification (HO)

Male and female C57BL/6 mice are used for the HO model. The HO is triggered by injecting BMP-2 into the muscle (Wosczyna et al. 2012).

All the mice are fed with standard feed and water ad libitum and are kept in groups of five mice per cage. The mice are exposed to a 12-hour light/dark cycle and air cooling to 23° C. (no special pathogen-free room). Enrichment is provided in the form of cardboard houses and bedding material. The mice are randomly divided into the different treatment groups and the assays are subsequently carried out as blind experiments.

The HO is examined by means of treatment using 2.5 µl of a 1 mg/ml recombinant BMP-2 solution (Thermo Fisher Scientific) or 2.5 µl of a 1 mg/ml Tfr2-ECD mixed with 47.5 µl Matrigel (BD Bioscience) at 0° C. For combination treatment, 2.5 of a 1 mg/ml recombinant BMP-2 solution is mixed with 2.5 µl of a 1 mg/ml Tfr2-ECD and 45 µl Matrigel. The Matrigel mixtures are injected into the musculus tibialis anterior of 10-week-old female wild-type mice. The legs are examined after two weeks.

µCT (Microtomography) and Bone Micromineralization Density

The bone microarchitecture is analyzed using vivaCT40 (Scanco Medical, Switzerland). The entire lower leg bones are measured at a resolution of 10.5 µm using X-rays of 70 kVp, 114 mA and at an integration time of 200 s. Predefined scripts from Scanco are used to analyze the bone (#1).

The mouse model of HO develops a BMP-2-induced ossification of the muscle tissue. FIG. 4 shows the inhibition of the ossification or HO in mice (C57BL/6 mice) by Tfr2-ECD, by means of binding of BMP-2.

Statistical Analysis

The data are specified as the average value±standard deviation (SD). Graphs and statistics are created using Graphpad Prism 6.0-Software. The normality of the data is determined by means of the Kolmogorow-Smirnov Test. In the case of normal distribution, statistical evaluations are carried out by means of two-sample comparison, using the Student's T-Test two-sample test. A one-way analysis of variance (ANOVA) is used for experiments having more than two groups. A two-way ANOVA comprising a Bonferroni post hoc test is used to analyze the treatment effects. If data do not correspond to the normal distribution, the Mann-Whitney U test and the Wilcoxon signed-rank test are used for the data analysis.

Non-Patent Literature Cited

Shore E M, Kaplan F S (2008) Insights from a rare genetic disorder of extra-skeletal bone formation, fibrodysplasia ossificans progressiva(FOP). Bone 43: 427-433.

Kölbl O, Barthel T, Krödel A, Seegenschmiedt M H (2003) *Prävention von heterotopen Ossifikationen nach Totalendoprothese des Hüftgelenks* [*Prevention of heterotopic ossification following total replacement of the hip joint*]. *Deutsches Ärzteblatt* [*German medical journal*] 45: 2944-2954. Baschant U, Sastre E A, Roetto A, Platzbecker U, Hofbauer L C, Rauner M (2017) P-OCBR-7: The iron-sensing receptor Tfr2 regulates osteoclastogenesis. Abstracts of the ECTS congress 2017. ECTS 2017. 13-16 May 2017, Salzburg, Austria. 44th European Calcified Tissue Society Congress: Page 43.

Roetto, A. et al. Comparison of 3 Tfr2-deficient murine models suggests distinct functions for Tfr2-alpha and Tfr2-beta isoforms in different tissues. Blood 115, 3382-3389, doi:10.1182/blood-2009-09-240960 (2010).

Wosczyna M W, Biswas A A, Cogswell C A, and Goldhamer D J (2012) Multipotent Progenitors Resident in the Skeletal Muscle Interstitium Exhibit Robust BMP-Dependent Osteogenic Activity and Mediate Heterotopic Ossification. J Bone Miner Res 27: 1004-1017.

LIST OF REFERENCE SIGNS

1 BMP
2 BMP-I
3 BMP-II
4 Tfr2α
5 protein
6 Smad protein
7 MAP kinase
8 phosphorylation
9 osteoblast genes
10 bone formation
11 capture antibody
12 detection antibody

---

The invention claimed is:

1. A method of treating a primary or secondary sclerosing disease in a subject, comprising administering to the subject a protein comprising the amino acid sequence of SEQ ID NO: 1, wherein the primary or secondary sclerosing disease is associated with increased Bone Morphogenetic Protein (BMP) receptor activation by at least one ligand selected from the group consisting of BMP2, BMP4, BMP6, and BMP7.

2. The method of claim 1, wherein the protein comprises the human transferrin receptor (Tfr) 2α comprising the sequence SEQ ID NO: 3.

3. The method of claim 1, wherein the protein is present in a pharmaceutical composition.

4. A method of treating a primary or secondary sclerosing disease in a subject, comprising administering to the subject a fusion protein comprising at least one protein comprising the amino acid sequence of SEQ ID NO: 1, wherein the primary or secondary sclerosing disease is associated with increased Bone Morphogenetic Protein (BMP) receptor activation by at least one ligand selected from the group consisting of BMP2, BMP4, BMP6, and BMP7.

5. The method of claim 4, wherein the protein is present in a pharmaceutical composition.

* * * * *

UNITED STATES PATENT AND TRADEMARK OFFICE
CERTIFICATE OF CORRECTION

| | | |
|---|---|---|
| PATENT NO. | : 11,878,048 B2 | Page 1 of 1 |
| APPLICATION NO. | : 16/622616 | |
| DATED | : January 23, 2024 | |
| INVENTOR(S) | : Rauner et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 478 days.

Signed and Sealed this
Fifth Day of November, 2024

Katherine Kelly Vidal
*Director of the United States Patent and Trademark Office*